(12) United States Patent
Karandikar

(10) Patent No.: US 9,757,387 B2
(45) Date of Patent: Sep. 12, 2017

(54) ANTIMICROBIAL COMPOSITIONS AND METHODS OF MAKING THE SAME

(71) Applicant: MEDICAL TECHNOLOGY RESEARCH INC, Woodburn, OR (US)

(72) Inventor: Bhalchandra M. Karandikar, Beaverton, OR (US)

(73) Assignee: Medical Technology Research Inc, Woodburn, OR (US)

( * ) Notice: Subject to any disclaimer, the term of this patent is extended or adjusted under 35 U.S.C. 154(b) by 0 days.

(21) Appl. No.: 14/652,730

(22) PCT Filed: Apr. 29, 2014

(86) PCT No.: PCT/US2014/035945
§ 371 (c)(1),
(2) Date: Jun. 16, 2015

(87) PCT Pub. No.: WO2014/179353
PCT Pub. Date: Nov. 6, 2014

(65) Prior Publication Data
US 2015/0313912 A1    Nov. 5, 2015

Related U.S. Application Data

(60) Provisional application No. 61/854,850, filed on May 2, 2013, provisional application No. 61/967,002, filed on Mar. 8, 2014.

(51) Int. Cl.
| | |
|---|---|
| *A61K 31/555* | (2006.01) |
| *A61K 47/02* | (2006.01) |
| *A61K 47/38* | (2006.01) |
| *A61K 47/10* | (2017.01) |
| *A61L 15/28* | (2006.01) |
| *A61L 15/20* | (2006.01) |
| *A61K 9/70* | (2006.01) |
| *A61K 9/06* | (2006.01) |
| *A61K 33/38* | (2006.01) |
| *A61K 9/00* | (2006.01) |
| *A01N 59/16* | (2006.01) |
| *A61F 13/00* | (2006.01) |
| *A61L 27/52* | (2006.01) |
| *A61L 27/54* | (2006.01) |
| *A61L 15/44* | (2006.01) |
| *A61L 15/46* | (2006.01) |
| *A61L 15/60* | (2006.01) |
| *A61L 26/00* | (2006.01) |

(52) U.S. Cl.
CPC .......... *A61K 31/555* (2013.01); *A01N 59/16* (2013.01); *A61F 13/00063* (2013.01); *A61K 9/0014* (2013.01); *A61K 9/06* (2013.01); *A61K 9/7007* (2013.01); *A61K 33/38* (2013.01); *A61K 47/02* (2013.01); *A61K 47/10* (2013.01); *A61K 47/38* (2013.01); *A61L 15/20* (2013.01); *A61L 15/28* (2013.01); *A61L 15/44* (2013.01); *A61L 15/46* (2013.01); *A61L 15/60* (2013.01); *A61L 26/008* (2013.01); *A61L 26/0066* (2013.01); *A61L 27/52* (2013.01); *A61L 27/54* (2013.01); *A61L 2300/104* (2013.01); *A61L 2300/404* (2013.01)

(58) Field of Classification Search
CPC ........ A01N 59/16; A01N 25/04; A01N 25/14; A01N 25/22; A01N 43/66; A61F 13/00063; A61K 31/555; A61K 33/38; A61K 47/02; A61K 47/10; A61K 47/38; A61K 9/0014; A61K 9/06; A61K 9/7007; A61L 15/20; A61L 15/28; A61L 15/44; A61L 15/04
See application file for complete search history.

(56) References Cited

U.S. PATENT DOCUMENTS

| | | | |
|---|---|---|---|
| 3,979,382 A | 9/1976 | Martinez-Alvarez et al. | |
| 4,136,177 A | 1/1979 | Lin et al. | |
| 4,136,178 A | 1/1979 | Lin et al. | |
| 4,288,430 A | 9/1981 | Etzel | |
| 4,364,929 A | 12/1982 | Sasmor et al. | |
| 4,708,821 A | 11/1987 | Shimokawa et al. | |
| 4,753,821 A * | 6/1988 | Giesecke ................. | G03C 5/58 427/304 |

(Continued)

FOREIGN PATENT DOCUMENTS

| | | |
|---|---|---|
| CN | 1672689 A | 9/2005 |
| CN | 101223116 A | 7/2008 |

(Continued)

OTHER PUBLICATIONS

Rao et al (Chem Communications, 2000, pp. 39-40).*

(Continued)

*Primary Examiner* — Mark V Stevens
(74) *Attorney, Agent, or Firm* — McCoy Russell LLP

(57) ABSTRACT

The present disclosure comprises antimicrobial compositions and devices comprising silver compounds that resist heat and light discoloration. In one aspect, the said compounds comprise silver and at least one s-triazine ring or moiety. In another aspect, the antimicrobial compositions are hydrogels that are effective against broad spectrum of common pathogens including MRSA and VRE and are suitable for treating human or animal wounds and burns. The methods of the present disclosure comprise treating medical and non-medical devices and articles with compositions comprising the silver compounds to impart antimicrobial property.

26 Claims, No Drawings

(56) References Cited

U.S. PATENT DOCUMENTS

| | | | |
|---|---|---|---|
| 4,900,561 | A | 2/1990 | Abdel-Monem et al. |
| 4,914,173 | A | 4/1990 | Ansell |
| 5,128,326 | A | 7/1992 | Balazs et al. |
| 5,158,772 | A | 10/1992 | Davis |
| 5,175,229 | A | 12/1992 | Braatz et al. |
| 5,759,410 | A * | 6/1998 | Christ, Jr. ............ C07D 251/38 210/711 |
| 5,804,213 | A | 9/1998 | Rolf |
| 6,333,054 | B1 | 12/2001 | Rogozinski |
| 6,342,212 | B1 | 1/2002 | Schuette et al. |
| 6,468,989 | B1 | 10/2002 | Chang et al. |
| 6,551,577 | B1 | 4/2003 | Chen |
| 7,129,375 | B2 | 10/2006 | Abdel-Monem et al. |
| 2006/0072444 | A1* | 4/2006 | Engel ........................ G11B 7/24 369/275.1 |
| 2007/0003603 | A1 | 1/2007 | Karandikar et al. |
| 2007/0134301 | A1 | 6/2007 | Ylitalo et al. |
| 2007/0254044 | A1 | 11/2007 | Karandikar et al. |
| 2008/0063693 | A1 | 3/2008 | Cook et al. |
| 2008/0149566 | A1* | 6/2008 | Messersmith ........ C09D 5/1662 210/702 |
| 2008/0200036 | A1* | 8/2008 | Stockum ................ C03C 15/00 438/756 |
| 2009/0035342 | A1 | 2/2009 | Karandikar et al. |
| 2012/0322903 | A1 | 12/2012 | Karandikar et al. |
| 2013/0052277 | A1 | 2/2013 | Weiss et al. |

FOREIGN PATENT DOCUMENTS

| | | |
|---|---|---|
| CN | 101588722 A | 11/2009 |
| JP | 4329146 B | 12/1968 |

OTHER PUBLICATIONS

Sodium Silicate 40%, Representative Website Available at http://cqconcepts.com/chem_sodiumsilicate.php, Website Available as Early as Feb. 24, 2006, Item First Observed 1640, 2 pages.

Vegetable Glycerin, Representative Website Available at http://www.lotioncrafter.com/glycerin.html, Website Available as Early as May 28, 2009, Item First Observed 1783, 3 pages.

Hydrogen Peroxide, 30% (Certifice ACS), Fisher Chemical, Representative Website Available at https://www.fishersci.com/shop/products/hydrogen-peroxide-30-certified-acs-fisher-chemical-6/p-213406#tab2, Website Accessed on Sep. 11, 2015, Item Available as Early as 1818, 4 pages.

Cyanuric Acid, Wikepedia Website Available at https://en.wikipedia.org/wiki/Cyanuric-acid, Website Available as Early as Sep. 13, 2006, Item First Synthesized 1829, 5 pages.

Fisherfinest Premium Plain Glass Microscope Slides, Representative Website Available at https://www.fishersci.com/shop/products/fisherfinest-premium-plain-glass-microscope-slides-2/p-45118, Website Accessed on Sep. 11, 2015, Generalized Version of Item Available as Early as 1839, 4 pages.

Vaseline Jelly Original, Representative Website Available at http://www.vaseline.us/product/petroleum-jelly/vaseline-jelly.html, Website Available as Early as Mar. 17, 2015, Item Introduced 1872, 8 pages.

Sodium Alginate, Sigma-Aldrich Product Specification, Available Online at http://www.sigmaaldrich.com/catalog/product/aldrich/w201502?lang=en&region=US, Website Accessed Sep. 11, 2015, Item First Described 1881, 1 page.

IKA High Shear Mixer, Representative Website Available at http://www.ikaprocess.com/Products/Inline-dispersers-Mills-dispersing-machine-high-shear-cph-6/, Website Available as Early as Nov. 2014, Generalized Version of Item Available as Early as 1885, 1 page.

Falcon Bacteriological Petri Dishes with Lid, Representative Website Available at http://www.fishersci.com/shop/products/falcon-bacteriological-petri-dishes-lid-4/p-88668#tab2, Website Accessed Sep. 11, 2015, Generalized Version of Item Available as Early as 1887, 3 pages.

Hydroxyethylcellulose (HEC), Representative Website Available at http://www.lotioncrafter.com/hydroxyethylcellulose-hec.html, Website Available as Early as May 27, 2009, Item First Observed 1905, 3 pages.

Ajinomoto Monosodium Glutamate, Representative Website Available at http://www.ajiusafood.com/products/flavor-enhancers/msg.aspx, Website Available as Early as May 9, 2010, Item Available as Early as 1909, 1 page.

Polyvinyl Alcohol, Sigma-Aldrich Product Specification, Available Online at http://www.sigmaaldrich.com/catalog/product/aldrich/341584?lang=en&region=US, Specification Date Apr. 27, 2011, Item First Described 1924, 1 page.

Desitin Maximum Strength Original Paste: Zinc Oxide Paste, Representative Website Available at https://www.desitin.com/diaper-rash-products/maximum-strength-original-zinc-oxide-paste, Website Accessed Sep. 11, 2015, Item Trademark First Use Aug. 12, 1932, 11 pages.

Brookfield DV-E Viscometer, Representative Website Available at http://www.brookfieldengineering.com/products/viscometers/laboratory-dv-e.asp, Website Available as Early as Mar. 23, 2006, Item Available as Early as 1934, 2 pages.

Gauze Pads BAND-AID Brand of First Aid Products Assorted Sizes, Representative Website Available at http://www.band-aidbrandfirstaid.com/first-aid-wound-products/covers-gauze-products/gauze-pads-band-aid-brand-first-aid-products-assorted, Website Accessed Sep. 11, 2015, Generalized Version of Item Available as Early as 1938, 5 pages.

Conical Centrifuge Tubes, 50 mL PP w/cap, Corning Life Sciences Customer Technical Data Sheet, Available Online at http://catalog2.corning.com/LifeSciences/en-US/Shopping/ProductDetails.aspx?productid=352070(Lifesciences) &categoryname=, Document Available as Early as Dec. 2013, Generalized Version of Item Available as Early as 1940, 2 pages.

TWEEN 20, Sigma-Aldrich, Representative Website Available at http://www.sigmaaldrich.com/catalog/product/sigma/p2287?lang=en&region=US, Website Available as Early as Apr. 30, 2012, Item Trademark First Use Apr. 25, 1941, 3 pages.

NE1540 Commercial Microwaves—Panasonic, Representative Website Available at http://www.panasonic.com/uk/consumer/home-appliances/microwaves/commercial-microwaves/ne-1540bpq.html, Website Available as Early as Mar. 28, 2014, Generalized Version of Item Available as Early as 1946, 3 pages.

Maxorb Extra Ag+ CMC / Alginate Dressings, Representative Website Available at https://www.medline.com/sku/item/MDPMSC9412EP?skuIndex=S1&question=&flowType=&indexCount=, Website Accessed Sep. 11, 2015, Generalized Version of Item Available as Early as 1948, 2 pages.

Methocel Cellulose Ethers, Representative Document: Dow Chemical "Methocel Cellulose Ethers Technical Handbook" Available Online at http://www.dow.com/dowwolff/en/pdf/192-01062.pdf, Sep. 2002, Item Trademark First Use Dec. 20, 1948, 32 pages.

Saran Premium Wrap, Representative Website Available at http://www.saranbrands.com/saran-wrap/, Website Available as Early as Nov. 4, 2005, Generalized Version of Item Introduced 1949, 2 pages.

Bounty Basic Paper Towels, Representative Website Available at http://bountytowels.com/en-us/shop-products/paper-towels/basic, Website Available as Early as Feb. 19, 2009, Generalized Version of Item Introduced 1965, 3 pages.

Sodium Polyacrylate, Wikepedia Website Available at https://en.wikipedia.org/wiki/Sodium_Polyacrylate, Website Available as Early as Dec. 15, 2005, Item First Synthesized 1966, 2 pages.

Rynel Hydrophilic Polyurethane Foams, Representative Website "Rynel: Foam Follows Function" Available Online at http://rynel.com/medical.html, Website Available as Early as Oct. 2, 1999, Rynel Founded 1973, 2 pages.

Seifer, G. et al., "Reactions in the AgNO3—NaxH3—xC3N3O3—H2O (x=1, 2, 3) Systems," Russian Journal of Inorganic Chemistry, vol. 34, No. 7, Jul. 1989, 4 pages.

Rheometrics Fluids Spectrometer II, Representative Website Available at http://www.plmsc.psu.edu/felix/Colby/research/RFS-II.html, Website Accessed Sep. 11, 2015, Generalized Version of Item Available as Early as Oct. 6, 1989, 1 page.

(56) References Cited

OTHER PUBLICATIONS

Natrosol Hydroxyethylcellulose, Representative Website Available at http://www.ashland.com/products/natrosol-hydroxyethylcellulose, Website Available as Early as May 21, 2011, Item Tradmark First Use Nov. 20, 1991, 2 pages.
Dermacea USP Type VII Gauze by Covidien, Representative Website Available at http://www.medline.com/sku/item/MDPKDL441203?skuIndex=S1&question=&flowType=&indexCount=, Website Accessed Sep. 11, 2015, Item Trademark First Use Nov. 22, 1994, 2 pages.
Tecophilic TPU, Representative Website Available at http://www.lubrizol.com/LifeScience/Products/Tecophilic.html, Website Available as Early as Dec. 26, 2013, Item Trademark First Use Jul. 15, 1996, 1 page.
Acticoat, Representative Website Available at http://www.smith-nephew.com/key-products/advanced-wound-management/acticoat/, Website Available as Early as Oct. 28, 2012, Item Trademark First Use Nov. 20, 1997, 3 pages.
Geliperm Sheet, Representative Website Available at http://www.dressings.org/Dressings/geliperm.html, Website Available as Early as Dec. 16, 1997, Item Disclosed as Early as Dec. 16, 1997, 3 pages.
Flexigel Sheet, Representative Website Available at http://www.smith-nephew.com/professional/products/advanced-wound-management/other-wound-care-products/flexigel-sheet/, Website Available as Early as Jul. 30, 2014, Item Trademark First Use Jul. 8, 1998, 2 pages.
Seifer, G., "Cyanuric Acid and Cyanurates," Russian Journal of Coordination Chemistry, vol. 28, No. 5, May 2002, 24 pages.
SilvaSorb Antimicrobial Wound Gel, Representative Website Available at https://www.medline.com/sku/item/MDPMSC9301EP;ecomsessionid=wQJO66OWa-TIH+qL-sZIQA_?skuIndex=S1&question=&flowType=&indexCount=, Website Accessed Sep. 11, 2015, Item Trademark First Use Aug. 23, 2002, 2 pages.
Peroxydone Complexes, Representative Website Available at http://www.ashland.com/products/peroxydone-complexes, Website Available as Early as May 21, 2013, Item Trademark First Use Mar. 25, 2003, 2 pages.
Curad Silver Solution Wound Gel, Representative Website Available at https://www.medline.com/sku/item/MDPCUR45951N?skuIndex=S1&question=&flowType=&indexCount=, Website Accessed Sep. 11, 2015, Item Available as Early as Oct. 19, 2004, 1 page.
Elta Dry Hydrogel Dressings, Representative Website Available at http://eltawebstore.com/wound_therapy/elta_hydrovase_gel/elta_dry_hydrogel_4_X_4, Website Accessed Sep. 11, 2015, Item Available as Early as Aug. 11, 2005, 2 pages.
Antimicrobial Silicone Dressings, Representative Website Available at http://www.covalon.com/antimicrobial-silicone-dressings, Website Available as Early as Oct. 1, 2011, Item Disclosed as Early as Aug. 29, 2007, 2 pages.
Silver-Sept Antimicrobial Skin and Wound Gel by Anacapa Technolo, Representative Website Available at http://www.medline.com/sku/item/MDPIDMQD3015S;ecomsessionid=mIY7psYjq-B1SnAURoE9Mig_?skuIndex=S1&question=&flowType=&indexCount=, Website Accessed Sep. 11, 2015, Item Trademark First Use Sep. 7, 2007, 2 pages.
Sun, X. et al., "N-Chloro-alkoxy-s-triazine-Based Antimicrobial Additives: Preparation, Characterization, and Antimicrobial and Biofilm-Controlling Functions," Ind. Eng. Chem. Res., vol. 48, No. 2, Jan. 21, 2009, Available Online Dec. 3, 2008, 6 pages.
Mahapatra, S. et al., "Silver Nanoparticle in Hyperbranched Polyamine: Synthesis, Characterization and Antibacterial Activity," Materials Chemistry and Physics, vol. 112, No. 3, Dec. 20, 2008, 6 pages.
Normlgel Ag, Representative Website Available at http://www.molnlycke.com/advanced-wound-care-products/antimicrobial-products/normlgel-ag/#confirm, Website Available as Early as Jul. 24, 2014, Item Available as Early as Sep. 13, 2011, 2 pages.
Harper, B. et al., "Boric Acid Technical Fact Sheet," National Pesticide Information Center, Oregon State University Extension Services, Available Online at http://npic.orst.edu/factsheets/borictech.pdf, May 2012, 14 pages.
ISA Korean Intellectual Property Office, International Search Report and Written Opinion Issued in Application No. PCT/US2014/035945, dated Sep. 12, 2014, WIPO, 12 pages.
State Intellectual Property Office of the People's Republic of China, Office Action and Search Report Issued in Application No. 201480010338.3, Apr. 12, 2017, 17 pages.

\* cited by examiner

ANTIMICROBIAL COMPOSITIONS AND METHODS OF MAKING THE SAME

CROSS-REFERENCE TO RELATED APPLICATIONS

The present application is a U.S. National Phase of International Application No. PCT/US2014/035945, entitled "ANTIMICROBIAL COMPOSITIONS AND METHODS OF MAKING THE SAME" filed Apr. 29, 2014, which claims priority to U.S. Provisional Patent Application No. 61/854,850, entitled "ANTIMICROBIAL COMPOSITIONS AND METHODS OF MAKING THE SAME" filed on May 2, 2013, and U.S. Provisional Patent Application No. 61/967,002, entitled "ANTIMICROBIAL COMPOSITIONS AND METHODS OF MAKING THE SAME" filed on Mar. 8, 2014, the entire contents of each of which are hereby incorporated by reference for all purposes.

FIELD

The present disclosure broadly pertains to antimicrobial compositions and devices comprising silver and specifically compositions for treating wounds and burns and the methods for making them.

BACKGROUND AND SUMMARY

To promote faster healing of infected wounds and burns, reduction of bio-burden is the first step. In quantitative terms, the bio-burden of infected wounds can reach as high as a million colony forming units (cfu) per gram of tissue. Therefore, rapid disinfection of the wounds followed by maintenance of low bio-burden is particularly attractive.

The most widely accepted clinical practice for reducing the bio-burden of the wounds is to cover them with dressings infused with antimicrobial compounds. The choice of wound dressing is dependent on the state of the wound; for badly infected wounds the dressings that release antimicrobial actives to the wounds very rapidly are preferred to cause bacterial count to drop to negligible levels. Thereafter, with optimal moisture management the body's immune system takes over to accelerate healing. A commercial product, Acticoat® is one such dressing that rapidly releases a lethal bolus of ionic silver. While such burst of ionic silver kills bacteria, it also stains skin and in the short term often retards wound healing.

Alternately, there are products that deliver the antimicrobial actives to the wound site more slowly over time. In such case, the bio-burden decrease takes place slowly but without interference with the body's natural healing process. Additionally, these products are compounded with agents that aid healing and provide for moisture management. Examples of such products include antimicrobial hydrogels (SilvaSorb®, SilverSept®, Normlgel Ag® and Elta®) and antimicrobial sheet dressings (SilvaSorb® and Covalon®)

However, in these products, especially the hydrogels, the amount of active silver compound is kept low so that in topical use they are not toxic to the skin cells. In hydrogels, due to their complex compositions and high viscosities, lower amounts of the silver compound often leads to uneven performance because the active species ($Ag^+$ ions) is sometimes prematurely reduced to elemental silver ($Ag^0$) which is inactive against microorganisms. The premature reduction often occurs in the hydrogel compositions in packaged form during storage due to various factors such as interaction with packaging material and changes in environment conditions. Thus, the silver containing compositions currently on the market perform differently when made fresh and may fail as they approach the end of their shelf life. To compensate for decreased activity of the hydrogel product nearing its end of useful life, the formulators often increase the amount of active ionic silver. However, increased amounts of ionic silver in the hydrogels increases the risk of premature reduction due to various factors mentioned earlier. The reduction of the active silver compound to inactive elemental silver in hydrogel compositions is accompanied by undesirable discoloration. In some situations, the hydrogels undergo a change in gel pH to acidic resulting in increased stinging and irritation to the patient's skin. This particularly is extremely undesirable to persons with sensitive skin or those with burns.

While some silver containing antimicrobial products such as Acticoat® dressings are dark colored and have been acceptable, consumer preferences do not permit dark colored or discolored hydrogels. Thus, antimicrobial compositions, particularly hydrogels that carry greater amounts of active silver compound(s) and yet are not dark colored when made or darkened prematurely in the packaged form may be useful. Furthermore, antimicrobial compositions that possess pH near neutral and are robust against pH drift into the acidic range may also be useful. In addition, antimicrobial hydrogel compositions that are clear to aid in the monitoring of healing wounds and that are able to provide moisture management may provide further utility in practice.

To provide a robust and effective antimicrobial hydrogel composition starts with a robust and effective antimicrobial active agent. Among the actives, in theory silver is quite effective because at therapeutic use levels it is non-toxic and there is history of its safe use among clinicians for over hundred years. Besides, there is practically no risk of common pathogens developing resistance to silver due to its multi-prong disruption of the bacterial growth cycle. In contrast, the popular antibiotics are already becoming ineffective as resistant strains of microorganisms are slowly emerging, which is an unintended outcome of their overuse. Other antimicrobials such as biguanides and chlorohexidine compounds may be potentially useful but they have toxicity issues and so may not work well.

However, despite the promise of silver, products with silver have not been as widespread in use. That's because an overwhelming majority of silver compounds are prone to heat and light induced discoloration and hence are not robust. Often those that are sufficiently resistant are sparingly soluble in water, e.g., silver sulfadiazine. For example, since the introduction of silver sulfadiazine forty years ago, there have been no reports of any silver chemistry that have matched or exceeded its discoloration resistance. Because of poor solubility in practically all solvents, silver sulfadiazine has been met with limited success. Given that there have been reports of silver sulfadiazine as not being as effective against microorganisms that have developed resistance to sulfonamides, going forward it is less likely to be the active silver compound of choice for device manufacturers and formulators. Further, the solubility problem in general can lead to product quality issues, which may increase use levels to achieve efficacy and therefore make manufacturing tricky. While there is no match to silver's broad spectrum efficacy, silver containing products when in contact with body parts or skin can cause staining Finally, the unpredictability of discoloration in silver containing devices may lead to poor yields in manufacturing, quality issues and a short shelf life. Various approaches to stabilization of silver in devices and compositions have been developed, but they have had limited utility due to their device specificity and limited implementation. Thus, an antimicrobial silver compound or a group of compounds that can provide more broadly robust resistance to heat and light induced discoloration and yet be relatively straightforward to incorporate into devices and compositions including hydrogels is lacking.

The inventor has recognized these issues and herein describes antimicrobial compositions that comprise silver cyanurate derivatives that hitherto were not investigated as antimicrobial actives. Antimicrobial devices comprising said compounds are also contemplated by the present disclosure. In one example, the antimicrobial compositions are hydrogels. The hydrogels are smooth, viscous, thixotropic, clear to translucent, readily spreadable under shear forces generated in topical use. Features of said antimicrobial compositions are clarity, ability to resist light and heat induced discoloration despite comprising active silver compounds at higher loadings. Some example hydrogel embodiments of the present disclosure are able to resist discoloration due to sunlight exposure or elevated temperatures of steam sterilization without compromising antimicrobial activity. The ability of said hydrogel compositions to withstand sunlight and elevated temperatures without discoloration while maintaining its antimicrobial effectiveness is a distinguishing feature of the present disclosure. Put another way, the robust thermal stability of said hydrogels precludes special storage conditions or shipping requirements and translates into practically an indefinite shelf life.

The antimicrobial hydrogel compositions of the present disclosure are non-staining to the skin and at use levels envisioned non-toxic to humans and animals. They possess effective broad spectrum antimicrobial activity against substantially all common pathogens: bacteria including MRSA and VRE, yeasts and fungi, but at higher silver loadings may be effective against, amoeba, protozoa, virus, etc. The said hydrogel compositions are suitable for use in the treatment of acute and chronic wounds that diabetics suffer, first and second degree burns and wounds on mucous membranes. When compounded appropriately they are effective and safe OTC products to treat minor cuts, burns and abrasions with minimal risk of staining. The hydrogels promote and accelerate wound healing by reducing bio-burden and promoting moisture management of low to moderate exuding wounds.

The present disclosure further provides methods of using a group of silver cyanurate compounds as antimicrobials. The compounds are inert to heat (steam sterilization temperatures) and light (direct sunlight), relatively easy to synthesize and incorporate into compositions and devices. To impart antimicrobial properties to compositions, they are derived simply by reacting metal cyanurates with soluble silver salts in solutions in situ or formed separately either individually or as a mixture and then compounded. Though sparingly soluble in water, when compounded into antimicrobial hydrogels at effective use levels, surprisingly they do not adversely affect gel transparency. Methods of making antimicrobial devices and compositions comprising said compounds for use as wound care products or patient care products are contemplated by the present disclosure. Examples of non-medical devices and their applications are provided.

DETAILED DESCRIPTION

The above advantages and other advantages, and features of the present description will be readily apparent from the following Detailed Description. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

Antimicrobial compositions that comprise silver are contemplated. The compositions are amorphous topical formulations that are suitably effective as broad spectrum antimicrobials against substantially all common pathogens: bacteria (gram positive and gram negative), anaerobes, yeasts and fungi. Though said compositions are contemplated for topical use, their use on mucous membranes in humans and animals, e.g., buccal cavity, is within the scope of the present disclosure. Depending on the amount of the antimicrobial active silver compounds in the compositions, they may also be effective against other organisms such as viruses, amoeba, protozoa, etc.

Antimicrobial Hydrogel Compositions

In one example, the compositions of the present invention are hydrogels, though other forms ranging from dilute suspensions (very low viscosity) or solutions to concentrates or dough-like compositions (extremely high viscosity) are not outside the scope of the present disclosure. As hydrogels, they are amorphous and therefore intuitive to use in any topical application. In one aspect, the compositions are thixotropic gels and possess yield stress. Such gels exhibit a rapid decrease in apparent viscosity when disturbed by stirring or even vigorous shaking. However, when the disturbance is removed, the apparent viscosity is restored and maintained during the dormancy state. The yield stress is the value that is overcome for transition from the gel (structured state) to sol (the flow or unstructured state) and dictates the ease with which the gel compositions can be spread. In one aspect, the hydrogel compositions of the present disclosure possess yield stress that range between 0 and 1000 Pa at 20-25 C, more preferably between 5 and 750 Pa and most preferably between 50 and 400 Pa. In addition, low yield stress permits ease of dispensing from packaged tubing. As described herein, the clear topical hydrogel may comprise an antimicrobial compound comprising silver and an s-triazine ring. In one example, the clear topical hydrogel may comprise hydrogen peroxide in addition to the silver cyanurate active agent. In some topical applications, the hydrogel is a thixotropic hydrogel and may have a yield stress in a range of 0 and 1000 Pa.

Another attractive property of the hydrogel compositions is the transparency. This attribute is desired by clinicians as it allows them to monitor from outside (through a thin film moisture permeable dressing) the progress of wound healing without having to resort to painful (to the patient) dressing changes to examine wound shrinkage. Interestingly, the transparency in the hydrogels is maintained despite the presence of active silver compounds to levels as high as 1000 ppm. Considering that the silver actives of the present disclosure are sparingly soluble in water the transparency observed in said hydrogels is quite remarkable.

The hydrogels of the present disclosure have low to moderate absorption characteristic that helps with moisture management of low to moderate exuding wounds. In heavily exuding wounds, excess moisture can often retard the healing process. Certain commercial products possess much higher absorption capacity compared to the hydrogels of the present disclosure. One embodiment of the present disclosure overcomes the limitation of moderate water absorption capacity of the present antimicrobial hydrogels. The embodiment utilizes a kit comprising the antimicrobial hydrogel (which can be sterile) and a sterile high water capacity bandage, e.g., a hydrophilic gel sheet or foam that in combination is used to effectively treat heavily exuding wounds. The high absorption capacity bandage helps maintain moisture in the wound while the antimicrobial silver hydrogel ensures a bacteria free environment, thus accelerating wound healing.

Certain wound hydrogels on the market contain microparticles of cross-linked hydrophilic polymer to enhance water absorption capacity. However, they are grainy to feel and often leave gel residue on the skin. In contrast, the present hydrogels are smooth to feel and can be rubbed into the skin akin to vanishing creams. This feature is quite relevant for OTC products meant to treat minor cuts, burns or abrasions because the presence of product residue is not desired by young patients who are end users.

Unlike some antimicrobial hydrogels on the market, the antimicrobial hydrogels of the present disclosure possess pH near neutral (7-8 range) and maintain their pH reasonably stable. They typically are free from the problem associated with stinging of skin caused by acidic pH. If incorrectly formulated, hydrogel products can cause pH drift into acidic 5-6 range over time. To mitigate the risk associated with stinging caused by acidic pH from ever happening with the antimicrobial hydrogels of the present disclosure, adding a painkilling compound, e.g., from the benzocaine family is within the scope of the present disclosure. But depending on the application, the hydrogel compositions may possess pH between 2 and 10. Such variations are also contemplated by the inventor. For instance, the compositions with acidic pH (5 or less) may be preferred in the treatment of fungal infection of nails.

For any topically applied antimicrobial product over the breached skin, the toxicity is of concern. Repeated use can cause the active compound to enter the body and do unintended harm. In the wound environment, the active levels can interfere with biochemical processes associated with healing. The antimicrobial hydrogels of the present disclosure incorporate silver compounds as active agents that are relatively safe at the levels contemplated for a wound care product intended for 3-5 days of use. In addition, the active silver compounds comprise moieties that have been used in commerce and have an acceptable safety record. For instance, the $LD_{50}$ value for rats in the case of cyanuric acid is 7700 mg/kg body weight (BW). In contrast, several common chemicals encountered in daily life such as boric acid (medicinal uses), benzoic acid or sodium benzoate (preservative) and salicylic acid (medicinal uses) have $LD_{50}$ (rats) values lower than that for cyanuric acid meaning they are more toxic. Further, the use of hydrogel compositions is primarily topical. Moreover, the compositions are viscous gels that offer a greater resistance to the diffusion of cyanurate anions or silver cations for entry into the body through breached skin. In this way, as one example, the amount of cyanuric moiety entering the body may be a thousand fold less than the toxicity threshold. As such, under extreme scenarios such as a condition where a burn victim has 40% body coverage with topical gel application that lasts over several days, the silver cyanurate derivatives may be considered practically non-toxic, even in such use levels contemplated by the present disclosure. As one example, identified use levels correspond to silver element equivalence of 2000 ppm or less with additional use levels being less than 1000 ppm. As another example, an amount of silver in the hydrogel may be between 50 and 1000 ppm based on a weight of the hydrogel.

The antimicrobial hydrogel compositions are suitable whenever there is sufficient need to provide antimicrobial conditions to sustain bacteria free environments. In a broader sense, the antimicrobial compositions provide an added layer of protection against bacterial or fungal contamination. They are especially useful in the treatment of (a) chronic and acute wounds and (b) first and second degree burns. For example, chronic wounds are characterized by a prolonged period of inflammation and delays in wound healing and repair, which often results from contamination by microorganisms. In contrast, heavily infected wounds have very high bio-burden with bacterial counts in excess of one hundred thousand cfu per gram of tissue. In both cases, the antimicrobial compositions provide therapeutic action by effectively eliminating or lowering bio-burden rapidly so that the body's natural healing processes can be initiated.

Because of the low to moderate thixotropic yield stress of the antimicrobial hydrogel compositions, they can be more easily applied as a thin layer under shear forces generated by fingers or hand. Thus, they are suitable for use to prevent infections on fresh burn skin areas characterized as $1^{st}$ and $2^{nd}$ degree burns without the risk of causing excruciating pain to the subject. When compounded to lowest effective silver levels in said compositions they can be used to treat minor cuts, abrasions and burns. As an added benefit, the hydrogel compositions do not cause skin stain even when applied areas are exposed in the daylight. This aspect can be valuable in an OTC product because kids often suffer such injuries playing outside and applying the compositions over injured areas would not preclude play activity because of fear of skin staining. In hospital settings, they are suitable to use without the risk of staining of patient garments, bed sheets and mattress coverings.

The medical applications of the antimicrobial hydrogel compositions comprising silver extend beyond wound healing. For example, the antimicrobial formulations with pH (5 or less) may be useful in the treatment of fungal infections of the nail and nail bed (onychomycosis) by eliminating causative dermatophytes. Alternately, embodiments of the present disclosure may be used to treat dermal conditions such as acne, rosacea, jock itch, and athlete's foot caused by the anaerobic bacteria (acne), demodex mites (rosacea), and fungi (jock itch and athlete's foot). Another embodiment of the antimicrobial compositions is as an ultrasound gel used in pregnancy monitoring. The compositions can render the applied skin area bacteria free during checkup and can have sufficient sound transmittivity due to the use of Laponite® synthetic clay as thickener. They can adequately replace current ultrasound gel products as they are also non-staining.

Besides hydrogels, other forms of amorphous compositions comprising active silver compounds are contemplated by the inventor. Suitable examples are suspensions, solutions, bioadhesive or adhesive compositions (U.S. Pat. No. 4,914,173), polymer solutions, lotions, creams, o/w or w/o emulsions, emulgels, salves, pessaries, ointments and sprayable liquids or suspensions (U.S. Pat. No. 6,551,577), latexes (U.S. Pat. No. 6,342,212), pastes, oily suspensions, water soluble polymeric films, water-insoluble films capable of sustained release of the antimicrobial agent and the like. Additional examples of amorphous compositions include various types of inks (e.g., flexo, gravure, inkjet inks for DOD and continuous ink jet) and aqueous and non-aqueous resins.

Antimicrobial Active Agents

The antimicrobial compositions of the present disclosure comprise antimicrobial active silver compounds. More specifically, the active compounds are a group of silver compounds comprising at least one s-triazine ring. Although those ordinarily skilled in the art recognize that silver containing compounds may have antimicrobial properties, not all compounds are suitable because they may lack the requisite light and heat stability. In that context, antimicrobial silver compounds comprising s-triazine rings is useful in that they are practically inert to light and heat typically encountered in the handling and/or manufacturing of antimicrobial compositions and devices. The relevant active silver compounds comprising the s-triazine ring are described in a published paper (see "Cyanuric acid and cyanurates" by Seifer G. B., Russian Journal of Coordination Chemistry, Vol. 28, No. 5, p 301-324 (2002) which is incorporated in its entirety by reference). Of those described, example compounds are listed in the table below. Hereafter, the silver compounds listed in Table 1 will be collectively referred to as "silver cyanurate derivatives".

TABLE 1

Silver cyanurate derivatives of the present disclosure

| S. No. | Silver Compound |
|---|---|
| 1 | $AgNO_3 \cdot C_3N_3 (NH_2)_3$ |
| 2 | $C_3N_3 (NH_2)_2NAg_2$ |
| 3 | Ammeline$\cdot AgNO_3$ |
| 4 | Ammelide$\cdot AgNO_3$ |
| 5 | Mono silver cyanurate ($C_3N_3H_2O_3Ag$) or its hydrate |
| 6 | Di silver cyanurate ($C_3N_3HO_3Ag_2$) or its hydrate |
| 7 | Tri silver cyanurate ($C_3N_3O_3Ag_3$) or its hydrate |
| 8 | Sodium silver cyanurate ligand complex $Na[Ag(C_3N_3H_2O_3)_2]$ or its hydrate |
| 9 | Potassium silver cyanurate ligand complex $K[Ag(C_3N_3H_2O_3)_2]$ or its hydrate |
| 10 | Mixed salt $NaAgC_3N_3HO_3$ or its hydrate |
| 11 | Mixed salt $NaAg_2C_3N_3O_3$ or its hydrate |
| 12 | Mixed salt $KAgC_3N_3HO_3$ or its hydrate |
| 13 | Mixed salt $KAg_2C_3N_3O_3$ or its hydrate |

Of the thirteen example compounds listed, the latter nine (No. 5 to No. 13) are highly effective example compounds with (i) Mono silver cyanurate ($C_3N_3H_2O_3Ag$) or its hydrate, (ii) Di silver cyanurate ($C_3N_3HO_3Ag_2$) or its hydrate, (iii) Sodium or Potassium silver cyanurate ligand complex Na or (K) $[Ag(C_3N_3H_2O_3)_2]$ or its hydrate, (iv) Mixed salt $NaAgC_3N_3HO_3$ or its hydrate and (v) Mixed salt $KAgC_3N_3HO_3$ or its hydrate being particularly attractive for further development.

Although some of the listed compounds have been known for over 175 years, those or others have not been suggested for use as antimicrobial agents because those ordinarily skilled in the art recognize that the overwhelming majority of silver compounds are light and heat sensitive and therefore reduce easily to elemental silver, which is known to cause brown black discoloration. Moreover, they also recognize there is no theoretical model to predict the degree of light and heat sensitivity of the vast number of silver compounds. Furthermore, the light and heat sensitivity of active silver compounds is attenuated in the presence of various other components more so in aqueous environments. Therefore, researching for robust silver compounds is more of an art and yet may benefit from a more scientific and systematic approach. For example, in the past forty years, only silver sulfadiazine, silver allantoin complex and to some extent silver saccharinate have been reported as known antimicrobial silver compounds with some inherent light and heat insensitivity. But higher insensitivity to light and heat of these silver compounds comes at the expense of solubility, which is extremely low in water. As a result, hydrogel compositions with very high levels of silver are difficult to formulate without rendering them opaque.

For the example compounds, either of the non-hydrated or hydrated form may be suitable without adverse effects on antimicrobial activity. In particular, one aspect of the present disclosure is that the silver cyanurate derivatives have been observed to be practically inert to light and heat. Perhaps because these compounds do not reduce easily and thereby resist discoloration by light or heat in an extraordinary manner. When subjected to intense light or extreme heat, the compounds are inert as dry solids and are also unaffected as aqueous suspensions or when dispersed in aqueous amorphous compositions. Thus, an object of the present disclosure is to provide antimicrobial silver compounds that are inert to light and heat as solids or when dispersed in liquids, or in semi-solids such as gels or dispersed in thin solid films such as dry coatings.

Another aspect of the present disclosure is to provide antimicrobial silver compounds that are sparingly soluble in aqueous or non-aqueous environments. These compounds are poorly soluble in water at room temperature and therefore release slowly. That allows for prolonged antimicrobial effect in devices and compositions. Due to low solubility, their effective concentration substantially always remains low thereby mitigating toxic effects. Yet due to silver's oligodynamic property, these compounds exhibit strong antimicrobial effects but remain non-toxic to the users. Despite their low water solubility, hydrogels comprising silver cyanurate derivatives have been formulated up to silver loadings of 1000 ppm without loss of transparency. For example, the amount of silver in the hydrogel may be between 50 and 1000 ppm based on a weight of the hydrogel.

Compounds comprising the s-triazine ring such as mono- or dichloro iso-cyanurates are known to have antimicrobial properties and have found commercial utility as disinfectants or sanitizers, but they exhibit significant toxicity. Yet, cyanuric acid, the starting material for the silver compounds of the present disclosure is considered relatively non-toxic and finds use as a stabilizer for N-chloro iso-cyanurates in pool cleaning compositions. According to an internet source (e.g., see www.wikipedia.org/wiki/Cyanuric_acid) the lethal dose LD50 for rats is 7.70 g/kg of body weight. Coupled with low toxicity of silver at therapeutically effective levels, the silver cyanurate derivatives of the present disclosure can be considered relatively safe. Furthermore, studies have shown the cyanurates are not metabolized and cleared from the human body within 24 h. Thus, another aspect of the disclosure is to provide antimicrobial silver cyanurate derivatives that are relatively non-toxic at use levels contemplated for antimicrobial devices and compositions for topical use.

With regard to the non-toxic nature of cyanuric acid just described (e.g., the lethal dose LD50 for cyanuric acid in rats is 7700 mg/kg of body weight), other example acids used in commercial applications are also known to have higher toxicities. For example, the lethal dose LD50 for boric acid in rats is 3450 mg/kg of body weight whereas the lethal dose LD50 for benzoic acid in rats is 2530 mg/kg of body weight; and the lethal dose LD50 for salicylic acid in rats is 1250 mg/kg of body weight. Guidelines provided by the US EPA establish toxicity classifications based on the amount of a substance within a test animal (e.g., rats, fish, mice, cockroaches). An LD50 is a standard measurement of acute toxicity that may be stated in milligrams (mg) of substance per kilogram (kg) of body weight. An LD50 represents the individual dose required to kill 50 percent of a population of the test animals. Thus, because LD50 values are standard measurements, comparisons may be made among various substances using their relative toxicities, and the lower the LD50 dose, the more toxic the substance. The LD50 may also be broken into additional categories that reflect the type of chemical exposure (e.g., Oral LD50, Inhalation LD50, and Dermal LD50). For example, toxicity classifications (and ranges) for the Dermal LD50 in rats are: high toxicity (LD50≤200 mg/kg); moderate toxicity (200 mg/kg<LD50≤2000 mg/kg); low toxicity (2000 mg/kg<LD50≤5000 mg/kg); and very low toxicity (5000 mg/kg<LD50). Thus, with an LD50 of 7700 mg/kg of body weight, cyanuric acid may be classified into the very low toxicity category based on the US EPA guidelines provided.

Syntheses of Antimicrobial Silver Cyanurate Derivatives

Another feature of the present disclosure is the relative ease with which the silver cyanurate derivatives can be synthesized thereby giving them an edge over competing products. Typical synthesis conditions are summarized in the accompanying Table 2. As noted, the silver cyanurate derivatives are obtained simply by combining stock solutions of ingredients in appropriate mole ratios. Due to their poor water solubility, the compounds precipitate out (typically as white solids) of the solutions, are washed multiple times with deionized water to remove side products and unused reactants. If desired the compounds can be recovered as solids after drying for further reformulation work.

TABLE 2

Details of synthesis of various silver cyanurate compounds @ 20-25 C.

| Compound | Silver nitrate (0.1M) [A] | Sodium cyanurate (0.1M) [B] | Order of addition |
|---|---|---|---|
| $C_3N_3H_2O_3Ag$ | 1 part | 1 part | B to A |
| $Na[Ag(C_3N_3O_3H_2)_2]$ | 0.5 part | 1 part | A to B |
| $C_3N_3O_3HAg_2$ | 1 part | 0.5 part (di sodium) | B to A |
| $NaAgHC_3N_3O_3$ | 1 part | 1 part | A to B |
| $C_3N_3O_3Ag_3$ | 1 part | 0.333 part (tri sodium) | B to A |
| $NaAg_2C_3N_3O_3$ | 1 part | 1 part | A to B |

Alternatively, the compounds can be formed in-situ into base amorphous compositions to introduce antimicrobial functionality. A distinct feature of their synthesis is the order in which reactants are added; it dictates which of the silver cyanurate derivative form. For instance, when an aliquot of monosodium cyanurate solution is added to an equal volume of silver nitrate solution of same molarity, monosilver cyanurate ($C_3N_3H_2O_3Ag$) hydrate is obtained. With the reverse order and the volume ratio of silver nitrate solution to monosodium cyanurate of 0.5, sodium silver cyanurate ligand complex $Na[Ag(C_3N_3H_2O_3)_2]$ is formed. Further approaching the ratio of cyanurate to silver ions of 1.0 from a value of 2.0, a solid phase rich in silver but with variable composition that includes $Na[Ag(C_3N_3H_2O_3)_2]$ is obtained. It is not very clear why such mixed composition solid phase is formed. But it appears that an excess of cyanurate anions continues to bind to the silver compound $Na[Ag(C_3N_3H_2O_3)_2]$ already formed giving rise to variable composition. This aspect occurs when mixing monosodium cyanurate and silver nitrate. However, no mixed phase solids result during the syntheses of di-silver or tri-silver cyanurate compounds. While collectively silver cyanurate derivatives are preferred, the solid product with variable composition comprising silver derived by adding stock solution of soluble silver salt to the stock solution of monosodium cyanurate in 1:1 mole ratio is also encompassed by the present disclosure. Similarly, solid products comprising silver obtained by mixing stock solutions of silver nitrate and ammonium cyanurate in no particular order are also within the scope of the present disclosure. The molarity of stock solutions of 0.1M in the syntheses described is for illustration and should not be construed as limiting. In fact the molarities can vary from 0.001 mM to 5.0M. Syntheses of silver cyanurate derivatives have been previously reported (see paper by Seifer G. B. and Tarasova, Z. A., Zh. Neorg. Khim., Vol. 34, pp. 1840-43, 1989), which employed 10 mM solutions. The illustrative synthesis work was performed with monosodium and disodium cyanurate, though similar steps are involved with trisodium cyanurate. An alternative procedure for making trisodium cyanurate was reported elsewhere (Japanese Patent No. 6829146 as cited in Chemical Abstract Volume 70: P78014 and incorporated here in its entirety by reference). In the syntheses described above, stock solution of silver nitrate was prepared in deionized water. Thus, the pH was substantially neutral (~7). However, the stock solution may be kept slightly acidic (pH 2-7 range) using an acid, wherein nitric acid is one example. Similarly slightly alkaline stock solution of alkali metal cyanurates may also be used in the above syntheses. Both of these variations of the preparation of silver cyanurate compounds are encompassed by the present disclosure.

In one aspect of the present disclosure, individual antimicrobial silver cyanurate compounds listed in Table 1 are contemplated for use in practice. However, they can be either employed singly or as a mixture of two or more compounds without departing from the scope of the disclosure. The use of mixed solid phase compounds obtained when the ratio of cyanurate ions to silver ions is between 1 and 2 also falls within the scope of the present disclosure. In fact, all silver cyanurate compounds formed as precipitates when the aqueous solutions of cyanurates (mono-, di- and tri-salt of alkali metals, alkaline earth metals, barium, magnesium, ammonium, copper, zinc and aluminum) and soluble silver salt such as silver nitrate are mixed are encompassed by the present disclosure regardless of whether they may be single chemical entity or a mixture of various entities. Furthermore, it should be recognized that the use of silver nitrate as a water soluble salt as a source of silver to prepare silver cyanurate derivative is merely for illustrative purposes and is non-limiting. For example, in one embodiment, silver salts that possess a moderate to high water solubility at 20-25 C of >5 g/liter is desirable. Though non-limiting, such example silver salts are silver acetate, silver lactate, silver citrate, silver sulfate and silver phosphate, with silver nitrate being useful for development according to the present disclosure.

While the active compounds contemplated for use in the antimicrobial compositions of the present disclosure are the silver cyanurate derivatives, said compositions may also comprise other silver compounds. These silver salts may or may not be sparingly soluble in water. For instance, additional example silver compounds are listed in the published US Patent Application No. US2007/0254044 which is incorporated here in its entirety by reference. As one example, said compositions may also include silver nanoparticles derived by methods disclosed in the published US Patent Application No. US2007/0003603. Any one of the silver cyanurate derivatives in Table 1 and any other silver compounds from those listed in the published US Patent Application No. US2007/0254044 or silver nanoparticles may be used in pairs or as multiple entity mixtures in hydrogel compositions to provide varying patterns of sustained release rates of silver ions for the desired therapeutic effect.

In another aspect of the present disclosure is provided the method of using alkali metal salts of cyanuric acid. For example, the use of alkali metals of sodium or potassium though lithium is contemplated. Other metal cyanurates (mono-, di- and tri-) of calcium, magnesium, barium, copper, zinc and aluminum are also encompassed by the present disclosure. In addition, the use of ammonium cyanurate and of mixed di-cyanurates (where the cations are dissimilar) is further contemplated by the inventor.

Though cyanurates of said metals are known, their commercial application has not been reported. In this context, their use as starting materials for a variety of silver cyanurate derivatives becomes a further aspect of the present disclosure. For example, one embodiment of the present disclosure is a mixed cyanurate salt of calcium and silver. Such salt can be used in the manufacture of antimicrobial alginate fibers. Another embodiment is the mixed cyanurate salt of barium and silver which can be incorporated into medical devices that provide dual function of anti-infectivity and of opacity to x-rays.

aqueous solutions. Silver ions are powerful oxidizers and therefore tend to reduce quickly even in presence of very weak electron donors. In the present case, without being bound to theory, the inventor further believes that free silver ions concentration in aqueous suspensions of any of the silver cyanurate compounds in Table 1 is extremely low. This can be deduced from the test observations (see Example 34) made with aqueous suspensions obtained by mixing monosodium cyanurate and silver nitrate solutions wherein the starting ratio of silver ions to cyanurate ions was as high as 8. At such a high ratio much in excess of stoichiometry, it was expected that considerable free silver ions would be present. As a result, after steam sterilization, the aqueous suspension would be discolored due to the reduction of free silver ions to $Ag^0$. But no such discoloration was observed suggesting that the majority of silver was bound to the cyanurate moiety as ligand complex (through N atoms) of unknown structure. At the same time, because of the retention of antimicrobial activity, one could deduce that the binding was not strong and was thus reversible.

TABLE 3

Observations on the crystals of silver cyanurate compounds

| S. No. | Compound | Water solubility (mg/L) | Morphology observed |
|---|---|---|---|
| 1 | $C_3N_3O_3H_2Ag$ | 243 | Two morphologies seen; majority nanofilaments and nanotrapezoids (<5%); filaments in 3 different sizes, majority 100-500 nm and 1-100 μm long |
| 2 | $C_3N_3O_3H_2Ag$ from ammonium cyanurate | Not Tested | Single: Nanorods with slant edges; dominant size: 100-400 nm ans 1-2 um long, minority size: 400-700 nm and 2-5 μm long |
| 3 | $Na[Ag(C_3N_3O_3H_2)_2]$ | 1.55 | Single; nanofilaments; 100-500 nm dia & 10-100 μm long |
| 4 | $C_3N_3O_3HAg_2$ | 851 | Single: Nanofilaments or rods; 50-100 nm dia & 500-800 nm long |
| 5 | $NaAgHC_3N_3O_3$ | 1.62 | Single: Short nanorods; 200-500 nm dia & 1-2 μm long that appear flat |
| 6 | Solid product from mixing 1 part $AgNO_3$ into 1 part Ammonium cyanurate | Not Tested | Two: one amorphous phase with pitted surface & nanorods; 1st kind 300-500 nm dia & 3-5 um long; 2nd: 50-200 nm dia & 1-2 μm long |

Mechanistic Aspect of Strong Light and Heat Discoloration Resistance

Without being bound to a theory, the inventor believes the reason behind unprecedented light and heat discoloration observed with the antimicrobial hydrogels comprising silver cyanurate compounds has to do with the sizes of the crystals of the silver active compounds formed within the hydrogels. The crystals are substantially of nano-dimensions (see Table 3 for summary of observations of the crystals of pertinent silver cyanurate compounds) that may allow the crystals to be intrinsically insensitive to light and heat. Further, the crystals do not readily agglomerate after they are formed perhaps because of the negative charge on the crystal surfaces. These charges are due to the ionization of the hydroxyl groups of cyanuric acid. As all particles carry like charges, they repel each other which in turn prevents the particles from coalescing and forming aggregates. The main causes of discoloration is the formation of elemental silver by the photo-reduction or thermally induced reduction of free silver ions, be so in hydrogel compositions or in simple Other Actives and Ingredients in Antimicrobial Compositions The compositions of the present disclosure may also comprise active agents such as antibiotic and biochemical compounds that may aid and/or promote wound healing. Non-limiting examples include growth factors, proteins, angiogenic factors, wound healing agents, growth promoters, enzymes, nutrients, vitamins, minerals, mucopolysaccharides, plant derived extracts or chemicals, herbicides, fats, carbohydrates, fatty acids, nucleosides, sera, amino acids, antibodies and fragments thereof, anesthetics, coagulations factors, vesicles with active agents, liposomes with actives including silver, neurochemicals, nitrates, antigens, cellular receptors, metal nanoparticles of silver, gold, copper, zinc, radioactive materials, anti-bacterial agents, antimicrobial agents (chlorohexidine and related compounds, biguanides and related compounds), anti-viral agents, anti-parasitic agents, anti-fungal agents (azoles and related derivatives), quaternary ammonium compounds, indicators of pH, oxidizing agents such as hydrogen peroxide, polyvinylpyrrolidone-peroxide complexes (Peroxydone® K-30 or K-90 ISP Corporation, Wayne, N.J.), organic (urea or melamine or cyanuric acid) and inorganic complexes of hydrogen peroxide (sodium carbonate and various other salts) or benzoyl peroxide. Alkali metal cyanurates and soluble silver salts may be added as dry solids without departing from the scope of the disclosure.

In addition to the antimicrobial silver active agent, hydrogels typically comprise a humectant, a single or multiple viscosity enhancing agent(s) and water as the major component. Optionally, they may comprise a biocompatible coloring agent, skin enhancing additives (e.g., essential oils, fragrances, moisturizing agents, emollients, toning agents, surfactants etc.) the use of which is known to those ordinarily involved in the topical formulation industry. Optionally, additives such as buffers to maintain a desired pH are also contemplated for use in said hydrogels. In this way, the methods described further comprise adding a buffer to the viscous gel and adjusting the pH of the antimicrobial composition to a range of 6 to 8. A variety of options for coloring hydrogels are also possible. The color may either be imparted by the use of traditional colorant (water soluble dye) or copper-amino acid complexes. Such complexes are known as the source of absorbent form of copper and find application as dietary food supplements in the animal feed industry (see U.S. Pat. Nos. 4,900,561 & 7,129,375 which are incorporated here in their entirety by reference). Moreover, FDA approved dyes for food industry and methylene blue may serve as suitable colorants. Glycerol, Propylene glycol, polypropylene glycols of varying molecular weights and urea are preferred as humectants though other humectants such as polyethylene glycols, sodium lactate etc. may also be used. Humectant action may be possible by using one substance or may be derived from two or more. The presence of humectants provides excellent moisturizing ability to the hydrogel compositions. Therefore, the methods described include making an antimicrobial composition with a silver cyanurate active agent. The method comprises combining a viscosity enhancing agent and a water based solvent to yield a viscous gel, and adding a metal cyanurate solution and a soluble silver salt solution to the viscous gel, where the metal cyanurate solution and the soluble silver salt solution react to form the silver cyanurate active agent. The method further comprises adding a humectant to the viscous gel, where the humectant is one or more of glycerol, propylene glycol, polypropylene glycol, urea, polyethylene glycol, and sodium lactate. In addition, the method may further comprise adding a coloring agent to the antimicrobial composition, where the coloring agent is one of a water soluble dye, a copper-amino acid complex, and methylene blue. In one example, the method further includes adding a skin enhancing additive to the antimicrobial composition, where the skin enhancing additive includes one or more of an oil, a fragrance, a moisturizing agent, an emollient, a toning agent, and a surfactant. The gel character of the hydrogels of the present disclosure is brought about by a synthetic clay mineral which hydrates when dispersed in water resulting in a very large increase in viscosity. One such clay is Laponite® from Southern Clay Products, Gonzales, Tex. Laponite® clay is the XLG grade. Though, its use is for illustration and is non-limiting. Alternately, natural clay minerals or mixtures thereof may also be included in the hydrogels. Other clay minerals that may be used for enhancing viscosity or imparting gel property are disclosed in columns 4 and 5 of U.S. Pat. No. 6,333,054 which is incorporated here in its entirety by reference.

To boost viscosity of the hydrogels is not limited to the use of natural or synthetic clay minerals. Other viscosity enhancing agents or thickeners may be used as well. Non-limiting examples include cellulose ethers (sourced from Ashland Chemical Company or Dow Chemical Company or others) such as hydroxyethyl cellulose, hydroxypropyl cellulose, hydroxyethyl or hydroxypropyl methyl cellulose, sodium carboxymethyl cellulose, polyacrylates (sources from Lubrizol Chemical Company and others), natural gums, chemically modified natural gums, chemically modified cellulose ethers with long chain aliphatic chains, synthetic gums, polyvinyl alcohol, polyvinyl pyrrolidone, polyacrylamide, polyaminoacids such as polyaspartate, polyglutamate and 2-acrylamido-2-methylpropane sulfonic acid (AMPS) derived polymers. As one example, polymers may be soluble in water and available in varying viscosity grades. The polymers may be used singly or as a mixture of more than one polymer. In addition, the viscosity increase in said hydrogels may be derived by using the clay mineral and polymer together.

For the delivery of the active silver, the compositions of the present disclosure may comprise hydrogels that have fluid absorbing property. They comprise hydrophilic polymers that swell by trapping water, saline or biological fluids within the polymeric free volume. They may reach an equilibrium absorption capacity (gm of water/gm of dry polymer) that ranges between 1.2 and 300.

The hydrogel compositions contemplated by the present disclosure may be neutral or ionic. A neutral hydrogel is substantially free of an electric charge and its pH is close to 7. Such neutral hydrogel may comprise moderate (~20,000) to high (~1,000,000) molecular weight PHMMA (polyhydroxyethyl methacrylate), polyvinyl pyrrolidone, polyvinyl alcohol with low acetate content, polyethylene oxide polymers with molecular weights up to ~5,000,000, polyvinyl ether polymers; cellulose ether polymers with degree of polymerization from 100 to 200,000 such as methyl cellulose, hydroxyalkylalkyl cellulose derivatives (ethyl hydroxyethyl cellulose, hydroxyethyl methylcellulose, hydroxybutyl methylcellulose, hydropropyl methylcellulose, hydroxyl ethylcellulose; neutral polysaccharides such as guar gum, locust bean and tamarind gum and the like. Hydrogels may be made from hydrophilic polymers made from monomers such as acrylamide, methacrylamide, N-substituted acrylamide, N-substituted methacrylamide and monomethacrylates of polyethylene glycols.

In contrast, the ionic hydrogel comprises polymers that have chemical groups which dissociate in aqueous media and become electrically charged. The ionic gels may be anionic or cationic. Non-limiting examples include gels derived from carboxymethyl cellulose polymers, copolymers of maleic acid with styrene, ethylene, propylene, butylene, isobutylene, N-vinyl lactam polymers, polyvinyl sulfonate polymers, phosphorylated hydroxyalkyl methacrylates, Carbopol® brand polymers, polyacrylic acid polymers and copolymers of acrylic acid with acrylamide or methacrylamide, methacrylic acid polymers, anionic derivatives of carrageenan, agar, Arabic gum, gum ghatti, and the like. Polymers derived from basic monomers such as aminoalkyl methacrylate, vinyl pyridine and other vinyl monomers carrying 5 or 6 member rings comprising carbon, nitrogen, sulfur and oxygen atoms. In some examples, when preparing hydrogels according to the present disclosure, combining cationic polymers with Laponite® clay material should be avoided.

A variety of chemical ingredients are suitable as additives in the antimicrobial compositions of the present disclosure. Non-limiting ingredients include cellulose ether polymers, sodium alginate, sodium alginate modified with small amounts of calcium or magnesium ions, propylene glycol or glycerol esters of alginic acid, gum karaya, guar gum, gum acacia, gum tragacatha as disclosed in U.S. Pat. No. 4,364,929 which is incorporated here in its entirety by reference. Additional examples of ingredients include hydratable polyurethane polymers (U.S. Pat. No. 5,175,229), gelatin and its derivatives, naturally occurring polymers and their derivatives (U.S. Pat. No. 5,804,213), proteins derived from corn or maize such as zain, hyaluronic acid and derivatives (U.S. Pat. No. 5,128,326), microbial polysaccharides such as beta-1, 3 glucan type polysaccharides (U.S. Pat. No. 5,158,772), polyvinyl alcohol derivatives (U.S. Pat. No. 4,708,821), xanthan gum (U.S. Pat. No. 4,136,177), locust bean (U.S. Pat. No. 4,136,178) and beta-cyclodextrin derivatives (U.S. Pat. No. 6,468,989), malodextrin and dextrin polymers.

In this way, the method further includes a viscosity enhancing agent selected from one or more of a synthetic clay mineral that includes Laponite®, a natural clay mineral, a cellulose ether selected from the group consisting of hydroxyethyl cellulose, hydroxypropyl cellulose, hydroxyethyl cellulose, hydroxypropyl methyl cellulose, and sodium carboxymethyl cellulose, polyacrylate, a natural gum, a chemically modified natural gum, a chemically modified cellulose ether with an aliphatic chains, a synthetic gum, polyvinyl alcohol, polyvinyl pyrrolidone, polyacrylamide, and a polyaminoacid that includes one of polyaspartate, polyglutamate and AMPS derived polymers. In addition, metal cyanurate solution may include one of sodium cyanurate, potassium cyanurate, lithium cyanurate, calcium cyanurate, magnesium cyanurate, barium cyanurate, copper cyanurate, zinc cyanurate and aluminum cyanurate. The soluble silver salt solution may further include one of silver nitrate, silver acetate, silver lactate, silver citrate, silver sulfate and silver phosphate.

With regards to the active agent, according to the methods of the present disclosure, the silver cyanurate active agent is one or more of $AgNO_3.C_3N_3(NH_2)_3$, $C_3N_3(NH_2)_2NAg_2$, Ammeline-$AgNO_3$, Ammelide-$AgNO_3$, Monosilver cyanurate ($C_3N_3H_2O_3Ag$), Disilver cyanurate ($C_3N_3HO_3Ag_2$), Trisilver cyanurate ($C_3N_3O_3Ag_3$), a sodium silver cyanurate ligand complex $Na[Ag(C_3N_3H_2O_3)_2]$, a potassium silver cyanurate ligand complex $K[Ag(C_3N_3H_2O_3)_2]$, a mixed salt of $NaAgC_3N_3HO_3$, a mixed salt of $NaAg_2C_3N_3O_3$, a mixed salt of $KAgC_3N_3HO_3$, a mixed salt $KAg_2C_3N_3O_3$, and a hydrated species thereof.

The water based compositions of the present disclosure particularly those suitable for medical purposes may comprise viscosities from about 1.0 centipoise (cP) to about 2,000,000 cP at 25 C and preferably from about 1 to 1,000,000 cP as measured on the Brookfield Viscometer. For those compositions that exhibit thixotropy, the yield stress as determined from frequency and strain sweep data may be about 1.0 Pascal (Pa) to about 10,000 Pa at 25 C.

The antimicrobial silver compositions, both aqueous and non-aqueous targeted for industrial uses may actually possess viscosities from about 0.0001 cP to about 2,000,000,000 cP at 25 C.

The water employed to produce hydrogels may be either deionized water or distilled water. Though desired that the water be pyrogen free, especially for medical purposes, it is not required. The non-aqueous compositions comprise non-aqueous solvents as a major constituent. Suitable examples include, acetone, methyl ethyl ketone, lower alkyl alcohols ($C_1$-$C_6$ carbon atoms) and their esters, cellosolve type solvents, THF, DMSO, DMF, propylene glycol, ethylene glycol, toluene and $C_5$-$C_{10}$ alkanes.

While the hydrogel compositions may be thixotropic, they also may or may not be thixotropic or clear or colorless or opaque. All such variations are encompassed by the present disclosure. While thixotropic character is a qualitative measure, the yield stress derived from established rheological measurement is quantitative and therefore represents a more robust metric of performance. In this way, hydrogels of the present disclosure possess yield stress values between 0 and 1000 Pa at 20-25 C, further between 5 and 750 Pa and further between 50 and 400 Pa. Besides hydrogels, the antimicrobial compositions of the present disclosure may take a variety of forms. They may be o/w emulsions or w/o emulsions or "emugels", salves, pessaries, jellies, creams, lotions, plain solutions and suspensions and may be so formulated to meet different customer requirements.

One embodiment of the present disclosure is an antimicrobial petroleum jelly with a silver content of ~540 ppm. It was derived by blending into plain petroleum jelly (Vaseline® brand obtained from a local store) a small aliquot of the suspension of silver cyanurate compound. The suspension of silver cyanurate compound was prepared by adding silver nitrate to monosodium cyanurate solution in 1:1 mole ratio, spiked with a small quantity of an emulsifier (e.g., Tween® 20, Sigma Aldrich). The resulting antimicrobial composition was smooth, opaque white, withstood continuous light exposure for a week without signs of discoloration and exhibited a zone of inhibition against *Staphylococcus aureus* ATCC 6538 in a ZOI assay. Such a composition could provide a sustained sanitizing effect compared to the alcohol based hand sanitizers and without the excessive alcohol induced dry feel.

Another example of antimicrobial composition of the present disclosure is a simple suspension of silver cyanurate compound. The suspension was prepared by simply mixing silver nitrate and monosodium cyanurate solutions (0.1M) in 1:1 volume ratio. When the molarity of the solutions is kept low, the resulting suspensions are actually clear and gives a hint of pearlescence. Moreover, these suspensions can be steam sterilized, are inert to light induced discoloration, have pH near neutral and have a practically indefinite shelf life given they are immune to environmental temperature changes. The ability to withstand steam sterilization cycles without a loss of antimicrobial effectiveness in aqueous medium and retention of its native white color distinguish the inventive compounds from the rest of the silver active compounds. This property is another feature of the present disclosure.

In an embodiment of the present disclosure, the suspension or solutions may be used as cleaning or sanitizing solutions in hospitals, ERs, surgical suits and in wound care. In yet another embodiment, the antimicrobial compositions (sterilized solutions or suspensions) comprising silver cyanurate compounds could be paired with a sterile absorbent gel sheet similar to a Flexigel® sheet as a wound care kit. The antimicrobial composition can be packaged in dark glass ampoules (as a precaution) and then steam sterilized. The gel sheet can be pouched in foil packaging and sterilized by e-beam or gamma irradiation. When used to cleanse the wound to reduce the bio-burden, the glass ampoule is broken and the sterile antimicrobial composition is poured into the pouch, left for few minutes to soak up the fluids. The now hydrated gel sheet is then removed from the pouch and applied to the wound that is bandaged up. In a modification of the embodiment disclosed here, the gel sheet could be replaced by an absorbent polyurethane sheet. Such foams are widely available commercially, e.g., from Rynel Inc. and Lendell Manufacturing Company, a unit of Filtrona Corporation, St. Charles, Mich. Polyurethane foams comprising various silver active agents (nanosilver, silver saccharinate) have been disclosed in the patent literature (US 2012/0322903 which is incorporated here in their entirety by reference). A Polyurethane foam comprising silver cyanurate compound can be prepared by following the procedure described in the US published Patent Application No. 2012/0322903 with small modifications. For instance, one can omit the solubilization step because the silver cyanurate compounds in suspension form as extremely fine particulates bordering on a colloidal state. Sterile solutions for treating ear infections represent another application where the simple liquid compositions of the present disclosure may be useful. The sterile solutions of silver cyanurate derivatives may also be used for sterilizing all types of orthopedic devices prior to implantation and may be an adequate substitute for the antibiotic cocktails currently employed. Furthermore, the sterile solutions or liquids comprising silver cyanurate derivatives may also be used to disinfect dental tools and may be suitable for use in dental implants to provide antimicrobial environment and prevent the growth of foul odor causing anaerobes in hard to reach gaps.

Another area where the liquid compositions of silver cyanurate compounds may find use is in negative pressure wound therapy (NPWT). Prior to use in NPWT, the sterile foam block may be wetted with sterile liquids comprising silver cyanurate derivatives. When in contact with the wound, silver in the liquids may rapidly diffuse to its surroundings, thereby killing the bacteria and reducing bio-burden. In this way, it may help lower the bio-burden, but it may further help control foul wound odors.

In yet another application of the liquid compositions comprising silver cyanurate compounds, they can be used in contact lens maintenance. An aqueous concentrate of the active compound or mixture thereof may be sterilized in a polypropylene bottle. A few drops of the concentrate may be added to the lens maintenance solution in the lens case to kill bacteria and prevent their growth. Due to silver's broad spectrum antimicrobial property it is also effective against amoeba some of which have been implicated in outbreak of infections among contact lens users. In another alternate application, the sterile solutions of the silver cyanurate derivatives may be used to disinfect drinking water. This application is more suited to emergencies or in developing countries. A few drops of aqueous concentrate comprising silver may be added to water to disinfect it and make is potable. Due to very low toxicity of cyanurate moiety, the risk to the users may be minimal and the benefit of using the same may far outweigh the potential harm caused by ingesting dirty water. The compounds can be added to liquid mixtures comprising water or non-aqueous solvents, o/w or w/o or w/o/w emulsions, emulgels, gels or suspensions. The fluid compositions may be used for disinfection of walls, floors, counters and table tops. It may be incorporated into cosmetics and surgical scrubs.

Another embodiment of antimicrobial aqueous compositions are water based paints such as acrylic paints. These paints include acrylic polymers that are normally water insoluble. Under alkaline pH, the acrylic acid groups of the polymers are converted to their ammonium salt. Into these paints, the silver cyanurate compounds can be formed in-situ or added as dry fine solids to impart antimicrobial function. Interestingly, not all of these active compounds are affected by pH >7. When surfaces are painted with such paints, the ammonia is lost to the atmosphere thus returning the acrylic polymer to insoluble antimicrobial paint layer. Such paints could be useful to keep the walls in operating rooms in hospitals germ free. Oil based paints may also incorporate the silver cyanurate derivatives without departing from the scope of the present disclosure.

A modification of the embodiment of antimicrobial paint is an antimicrobial sodium silicate composition comprising silver cyanurate compounds. In preparing such a composition, a suspension of silver cyanurate compound was blended into 40% by weight aqueous sodium silicate solution to obtain a milky viscous mixture. To simulate a real life application to a tiled surface, a glass slide was coated with the mixture that was cured at 110 C to form insoluble glass with finely divided trapped particles of the active compounds. The coating did not discolor after 30 days of continuous light exposure and exhibited antimicrobial activity in a ZOI assay.

In another embodiment, the silver cyanurate derivatives may be included in creams to treat diaper rash. As an example, a commercial diaper rash ointment was blended with silver cyanurate compound in a manner similar to that described earlier to prepare petroleum jelly. There was no visual difference between the ointment samples with and without silver. Though in ZOI assay, the ointment with silver showed a large inhibition zone consistent with its increased antimicrobial potency.

Another aspect of the present disclosure is to provide inert solid substrates of varying contents of silver cyanurate compounds. Such substrates may be powders both natural and synthetic or made of inorganic porous supports, ceramics, metals, oxides, pellets, short fibers etc. In preparing one such embodiment, talc powder was dispersed in a mixture of water and ethanol. To the suspension formed, monosodium cyanurate solution was added followed quickly by equal aliquot of silver nitrate solution to evenly precipitate out an insoluble fine silver cyanurate derivative compound. The talc powder with dispersed active compound was recovered after filtration, washing and dried. Visually, no difference was observed between dry talc with and without silver. Such silver impregnated talc could be convenient to use in the treatment of athlete's foot or to fight foot odors caused by bacteria. They may be also suitable for use by diabetics to prevent wound infection on feet.

Antimicrobial Medical and Non-Medical Devices

A large number of devices for use in medical industry and non-medical industry can be rendered antimicrobial using the amorphous compositions comprising the silver cyanurate derivatives. For example, coatings may be applied to surfaces of pre-made three dimensional objects or articles by traditional means such as dip coating, brushing or spraying. As such, the antimicrobial compound may be blended into a surface coating of a medical device. In other cases, the actives may be incorporated into pre-mixes and then the objects or articles molded into shapes. Suitable devices that can be imparted antimicrobial function by the silver cyanurate compounds of the present disclosure include air and water filtration devices, air ductwork, fan housings, aquarium filter material, automobile ventilation, air conditioner systems, bed sheets, blankets and bed spreads, buffer pads (abrasive and polishing), carpets and draperies, fiberfill for upholstery, sleeping bags, apparel, etc. where the fiber is cellulose (natural or regenerated), natural down, nylon, polyester, rayon, wool, fiberglass duct board, fiber hose fabric, humidifier belts, mattress pads, underwear and outwear, nonwoven disposable baby and adult diapers, tampons, nonwoven polyester, camp gear apparel, PU foam cushions, PU foam for household, industrial and institutional sponges and mops, PU foam for packaging and cushioning, PU foam as growth medium for crops and plants, pre-moistened towelettes and tissue wipes, roofing materials such as shingles, roofing granules, wood shakes, wood planks of various widths, lengths and sizes, felt, stone and synthetic overcoats, sand bags, tents, tarps, sails and ropes, athletic, casual and dress shoes, shoe insoles and inserts, leather and leather like products, shower curtains, socks for athlete's foot fungus control, throw rugs, towels made of 100% cotton or polyesters or their blends, toilet tank, toilet cleaning tablet and seat covers, umbrellas, upholstery made of acetates, acrylics, cotton, fiberglass, nylon, polyester, PE, polyolefins, PP, rayon, spandex, vinyl and wool, vacuum cleaner bags and filters, vinyl or wall papers, disposable wiping cloths for dusting and washing furniture, car, walls, windows, doors, appliances, dishes, counter tops etc. women's hosiery and women's intimate apparel. Additional industrial items include food packaging, drug and cosmetic packaging, eating utensils, shower curtains, bath mats and the like, compositions such as grout, cement and concrete to fight growth of mold and mildew, sponges, toilet seats, kitchen, bath or lab shelf paper, carpet pads, preservative packets for flower bouquets that may as one example be used to prevent and/or limit microbial growth within the bouquet, pool covers, solar pool covers, cat litter, animal bedding, individual computer keyboards and replacement keys, door knobs, tampons, sanitary napkins, dental chairs, dry sheets, mops and dishcloths, adhesives, silicone products (tubing, plugs, sheets etc.), and microbeads made from natural and synthetic polymers and friable beads. In this way, the antimicrobial compounds may be useful in non-sterile as well as sterile applications.

The medical devices suitable for imparting antimicrobial property utilizing the compositions comprising silver cyanurate derivatives include catheters, blood lines, metal or metal alloy implants and orthopedic devices, prosthetic devices and inserts, thermometers, bandages, surgical dressings, surgical apparel, face masks, respirators, wound care and ostomy products, rubber gloves, contact lenses, hearing aids, implantable hearing devices and dusting powder. Examples of fiber and fabric products contemplated include, but are not limited to surgical gauze, padding on wound dressings, mattress covers, crib covers, bassinet covers, sailboat sails, tents, draw sheets, cubicle curtains, tooth brushes, hair brushes, fabric wall coverings, fabric base, fabric shower curtains, bath mats, athletic clothing such as underclothes, shirts, socks, shorts, pants, shoes, hospital clothing such as examination robes, physicians coats and nurses uniforms, blood pressure measuring device etc. Additional examples of both medical and non-medical devices that can be rendered antimicrobial with the silver cyanurate derivatives of the present disclosure are listed in para [140] of US published Patent Application No. US 2007/0003603 which is incorporated here in its entirety by reference.

The silver cyanurate derivatives may be applied topically to both, natural or synthetic fiber or incorporated directly into the synthetic fibers during fiber manufacturing process. The fibers are not limited to wool, cotton, polyolefins, polyester, polyamides, cellulose acetate, rayon, polystyrene, vinyls, acrylics and PU's.

The antimicrobial medical and non-medical devices comprising the silver cyanurate compounds of the present disclosure may be sterilized by the known methods such as ETO, steam sterilization, E-beam and gamma irradiation. Even the antimicrobial amorphous compositions besides steam sterilization may be sterilized by E-beam and gamma irradiation at very low KGy dosages.

Methods of Making the Antimicrobial Compositions

Another aspect of the present disclosure include methods of making the antimicrobial compositions comprising the silver cyanurate compounds. One method comprises the steps of combining a viscosity enhancing agent or thickener, a humectant with deionized water to yield a viscous gel and adding successively to said gel metal cyanurate solution and a soluble silver salt solution to the active silver cyanurate compound in-situ. The step involving the soluble silver salt solution addition is carried out in the dark though it may be carried out under low lighting conditions without departing from the scope of the disclosure. The resulting composition is an antimicrobial hydrogel with pH in physiological range (6-8) that is thixotropic, spreadable, smooth, clear or transparent and moisturizing. Furthermore, the hydrogel and its variants have low to moderate capacity to absorb additional water which assists in the moisture management of the wounds. In another method to prepare said hydrogel, active silver cyanurate compound is pre-made as a milky white suspension by mixing appropriate volumes of equimolar monosodium cyanurate and soluble silver salt solutions and then blended in.

Some ingredients such as thickeners and humectants used in the preparation of said compositions are commercially available. Of those that are cosmetic grade or FCC/NF/USP grade are attractive for use. As to the source of the active silver, ACS grade soluble silver salts may be used though the high purity USP grade may also be used. Various alkali metal cyanurate compounds which are not commercially available are synthesized using cyanuric acid. First, commercial grade cyanuric acid is purified to remove acid soluble impurities followed by neutralization reaction with sodium hydroxide. When the acid and base are in 1:1 mole ratio, monosodium cyanurate is obtained which is recrystallized from water for further purity. Presence of additional sodium hydroxide yields di-sodium cyanurate. One can obtain tri-sodium cyanurate using large excess of sodium hydroxide as reported in the published literature. Similarly, one can obtain ammonium cyanurate crystals by simply combining a slight molar excess of ammonium hydroxide with cyanuric acid. In the preparation of alkali metal and ammonium cyanurate salts, it is desirable to heat the reaction mixtures to 80-85 C for 0.25 to 4 hours, however heating for 0.25-2 hours may also be used to drive the reactions to completion.

Various embodiments of the methods described above are possible with each of them encompassed by the present disclosure. For instance, in one embodiment of the method, the humectant is added in the last step. In a second embodiment, the thickener or viscosity enhancing agent and the humectant may be combined to from a viscous blend that is then hydrated with water and then the active compound is formed in-situ in the final steps. In a third embodiment, the active agent suspension is prepared and then diluted with water. The thickener e.g. Laponite XLG is hydrated into the diluted suspension and finally the humectant is added. Though each of the silver cyanurate compounds of the present disclosure are antimicrobial, which of them are formed in-situ in the hydrogel compositions or in suspensions is simply dictated by the order of addition of the reagent solutions and their volume ratio. In general, the hydrogel preparations of the present disclosure may be implemented with a wide range of the molarity of the metal cyanurates or soluble silver salt solutions. Thus, the molarity of the said solutions can be between 0.001 mM and 5M though values between 0.001M and 0.5M are also possible, and values between 0.05M and 0.2M are further possible.

In general, the methods of making hydrogels of the present disclosure contemplate the formation in the composition of one kind of active silver cyanurate compound. However, a method to make hydrogel with two or more active silver cyanurate compounds is not outside the scope of the present disclosure. For example, to the base gel comprising the thickener and humectant in water, one may add a suspension of mono-silver cyanurate and a suspension of di-silver cyanurate thereby deriving a hydrogel with two silver cyanurate actives. Optionally, other silver salts solutions may be added to yield different hydrogel compositions. Alternately, two or more actives may be formed in-situ in the base hydrogel (composed of thickener, humectant and deionized water). To those ordinarily skilled in the formulation industry, it will be apparent that a large number of permutations and combinations of the actives are possible with each considered within the scope of the present disclosure.

In another inventive modification of the hydrogel preparation, the use of metal cyanurate is omitted. In obtaining the finished hydrogel, the method comprises steps of (i) dissolving cyanuric acid in deionized water, (ii) dispersing and hydrating Laponite XLG clay to the acidic water, (iii) adding soluble silver salt solution in an amount corresponding to 1:1 mole ratio with the said acid and finally, (iv) adding the humectant.

In another embodiment of the method of making hydrogel composition, two thickening agents are separately dissolved in deionized water and then the solutions combined, followed by the humectant, and precipitation in-situ of the active silver compounds. The advantage of this embodiment is the reduction in the opacity of the finished hydrogel especially if one the thickening agent is a synthetic clay Laponite XLG.

The employment of the silver cyanurate compounds is not limited to imparting antimicrobial property to just hydrogel compositions. These compounds can efficiently be incorporated into aqueous and non-aqueous compositions, devices, objects and substrates such as paper and fibers.

One embodiment of the aqueous composition comprises a single active silver cyanurate compound suspended in water. Optionally the aqueous composition may include a biocompatible polymer such as polyethylene oxide polymer or polyvinyl alcohol of low to moderate molecular weight (MW: 20,000 to 200,000) to stabilize the suspension and prevent dense particles of the active silver compound from settling. The use of surfactants such as the Tween® or Span® family surfactant in the compositions to increase compatibility with hydrophobic constituents is also contemplated by the inventor. The amount of silver present in such compositions may be between 0.0001% and 1.0% by weight, but may also be between 0.002% and 0.8% by weight and may further be between 0.0025% and 0.5% by weight. The amount of polymer or surfactant can be between 0.001% and 10% by weight and but may also be between 0.005% and 1.0% by weight. The preferred polymer grade is USP. Other polymers such as cellulose ether polymers or polyvinyl pyrrolidone may also be used in such compositions and their use is within the scope of the present disclosure.

The following describes a method of making an embodiment in the form of a w/o emulsion or cream, where the oil phase is petroleum jelly and water phase comprises active silver cyanurate compound. The method comprises the steps of (i) preparing a suspension of the active silver cyanurate compound by admixing solutions of soluble silver salt and monosodium cyanurate, (ii) further adding to the suspension an emulsifier Tween 20 and dispersing the aqueous mixture into the petroleum jelly to produce whitish opaque cream. The same method may be employed to prepare a cream that may also comprise zinc oxide.

In an aspect of the present disclosure, a method is provided to impart antimicrobial properties to a paper substrate. The method may also be applied to render woven or non-woven fibrous material (derived either from natural or synthetic sources) antimicrobial especially those that are wetted by water or mixtures of non-aqueous solvents such as acetone, THF, and alcohols with water. The method comprises the steps of (i) adding soluble silver salt solution to mono sodium cyanurate wherein the cyanurate anion is in excess of silver ions, (ii) diluting the resulting suspension of the active silver cyanurate compound with dilute aqueous ammonia, (iii) dipping the non-woven substrate for time sufficient to allow for the substrate to absorb the fluids, (iv) squeezing out excess fluid and finally (v) drying the substrate to remove all residual solvents. In a variation of the above method, in the step (ii) instead of dilute ammonia one may use a non-aqueous solvent or a mixture of water miscible non-aqueous solvent and water wherein the non-aqueous solvent is more than 50% by volume.

The methods of making antimicrobial compositions of the present disclosure are quite versatile to implement. By simply adjusting the molarity and or the volume of soluble silver salt solution utilized one can tailor the desired amount of silver loading in the composition. Moreover, by selecting the order of addition of the two reagents—silver salt and alkaline cyanurate solution—one can choose the type of active silver compound desired in the composition. Further, one may incorporate a variety of active silver compounds, all with excellent antimicrobial effects simply by choosing either a mono-, di- or tri-sodium cyanurate or any other metal cyanurate as the anion exchanging compound.

Methods of Using the Antimicrobial Compositions

In one embodiment of the method, the hydrogel may be used to treat topical infection. The composition is generously applied to the infected area of the skin and appropriately to the surroundings and then covered with a dressing. In a modification of the method, the hydrogel with moderate level of silver may be used to treat infection in partial thickness or deep wound. The hydrogel in a quantity sufficient to be therapeutically effective is applied to the wound and the surrounding area and covered with a dressing. Optionally a sterile absorbent foam sheet dressing may be applied over the hydrogel to enhance exudate absorption. In another embodiment of the method, the hydrogels may be used to treat pressure ulcers, partial and full thickness wounds, diabetic foot and leg ulcers, graft and donor sites, and first and second degree burns. In yet another embodiment, the hydrogels with high levels of silver content may be used to reduce the bio-burden of gangrenous wounds followed by the use of low silver hydrogels to maintain the wound bacteria free and accelerate the wound healing processes.

A related embodiment of the method of treating infected wounds comprises a kit that includes a sterile antimicrobial aqueous suspension comprising silver cyanurate compounds (contained in an ampoule) of the present disclosure and a sterile hydrogel sheet contained in a pouch capable of absorbing fluids when contacted with infected wounds and the method of using the kit to treat infected wounds. The treatment comprises the steps of (i) breaking the ampoule and opening the pouch by aseptic means, (ii) combining the antimicrobial aqueous suspension by pouring into the pouch, (iii) maintaining intimate contact between the suspension and the said hydrogel sheet for sufficient time to absorb the fluids partially and coat the antimicrobial active on the said hydrogel sheet, (iv) removing the partially hydrated hydrogel sheet and placing it over the infected wound and finally (v) applying a dressing to cover the wound. Examples of hydrogel sheet suitable for use are Flexigel® and Geliperm® brand sheets. The method embodied in the invention may also utilize sterile non-woven alginate dressings or a hydrophilic PU foam or cotton gauze that do not possess antimicrobial property without departing from the scope of the present disclosure. The duration between dressings changes in practice and may be dictated by how long the antimicrobial effect is sustained, which in turn depends on the silver loading of the aqueous suspension. In one embodiment, silver loadings are those that sustain antimicrobial effect for three to seven days.

In hydrogel compositions wherein the silver loading levels are low, the antimicrobial effect may last a day or two. Such hydrogel compositions may be used to treat minor skin cuts or abrasions or very small area burns. For instance, a hydrogel bead is applied to the cut or burn and then covered with a bandage strip. Based on the ability of the hydrogel compositions of the present disclosure to resist light and heat induced discoloration, they may be applied on the skin without the risk of staining.

In yet another embodiment of the method, said hydrogel compositions may be used to treat dermal conditions such as acne, rosacea, jock itch, athlete's foot and onychomycosis (nail fungus infection) which are caused by a host of micro-organisms. The broad spectrum silver cyanurates are effective against causative agents for these dermal conditions, namely the anaerobic bacteria (acne), demodex mites (rosacea), fungi (jock itch and athlete's foot) and dermatophytes (onychomycosis). The silver content of antimicrobial compositions for treating acne, rosacea, jock itch, athlete's foot and onychomycosis is preferably between 0.01% and 0.3% by weight. To be effective in treating these dermal conditions, said compositions are applied evenly to acne pimples or the affected area in the case of rosacea and jock itch or athlete's foot. The affected nail bed is evenly covered with said compositions spread as a layer and covered with a dressing. The treatment durations in practice may vary depending upon the severity of the respective condition.

In another embodiment of the present disclosure is provided a method of preventing or inhibiting biofilm formation on a surface. The method comprises the steps of (i) preparing a coating solution comprising one or more active silver cyanurate compound, (ii) applying said coating solution to the surface, and finally (iii) drying the coating to remove solvent residues. The coating solution can be water based or can be made of non-aqueous solvents or mixtures and prepared by dissolving suitable polymers and adding a suspension of the active silver compound or forming the active compound in-situ. Any suitable hydrophilic polymer may be employed, including, for example, polyhydroxyethyl methacrylate, polyacrylamide, polydimethylsiloxane, N-vinyl-2-pyrrolidinone, hydrophilic polyurethane, and the like. The hydrophilic polymer may be hydrophilic polyurethane, such as the TECOPHILIC™. polyurethane sold by Thermedics of Woburn, Mass., for example. Examples of lipophilic polymers include silicone, polyurethane, polyethylene, nylon, polyvinyl chloride, polyvinyl alcohol, the cellulosic polymers, polyvinyl acetate, polyesters, and acrylics. For implants, the coatings are derived from bierodable polymers or bioabsorbable polymers which are known to those skilled in the art.

In another aspect of the present disclosure, the hydrogel compositions comprising silver cyanurate compounds with high silver content may serve as anti-viral compositions to treat and heal cold sores caused by herpes simplex virus. The compositions may be applied in small amounts to cover each sore. The active silver may neutralize the virus by attaching to viral proteins and thereby reduce its infectivity. In addition, it may also aid in healing the sore quickly by disinfecting the area. The antimicrobial hydrogel compositions for antiviral application comprise silver in the range of 0.005% and 5.00% by weight, however silver in the range 0.01% and 3.00% by weight may also be used, and silver in the range 0.1% and 0.5% by weight may be further used in some examples.

In another embodiment of the methods of the present disclosure, the hydrogel compositions are used to reduce the risk of infection to women due to HIV during sexual intercourse. Though, it has been reported that silver nanoparticles in concentration of ~1000 ppm can inhibit HIV, ionic silver present as salts was not found to be as effective. The effectiveness of silver nanoparticles against HIV inactivation was attributed to the nano dimensions of the particles that allowed their greater interaction with HIV. In contrast, because it is difficult to maintain ionic silver at high concentration in suitable vehicles such as gels as it deactivates rapidly by photo-reduction or is reduced by heat (visual indication is that it turns black or grey) previous silver compositions were ineffective. The antimicrobial hydrogel compositions cure this deficiency as they possess excellent stability against deactivation. In addition, the active silver cyanurate compounds in the hydrogel compositions have been observed by high resolution SEM to possess nano-dimensions that increase the probability of their lethal interaction with viruses. Furthermore, the hydrogel compositions are smooth, viscous, thixotropic, transparent, have pH in physiological range and are readily spreadable under shear forces generated in topical use and are convenient to use as a vaginal lubricant. As such, the hydrogel compositions may be applied to an uninfected individual to reduce the risk of infection due to HIV during sexual contact.

In one related embodiment of the disclosure, said compositions are provided in convenient single use disposal packets and can withstand the harsh environmental conditions of third world countries located in Asia and Africa. To reduce the risk of HIV transmitting to an uninfected female during sexual contact, said compositions are applied in sufficient amount to cover the vaginal area including folds prior to sexual contact. The risk of infection during sexual intercourse may be reduced as the silver may inactivate viral particles by attaching to electron donating groups present on viral proteins and so prevent viral replication.

In yet another embodiment, the silver cyanurate compounds of the present disclosure may be very fine crystalline materials having nano-size dimensions. Thus, their ease of preparation and uniformity and consistency of crystal morphology may further enable their use in security applications as taggants. For example, the compounds can be radioactive and so derived from the combination of a metal cyanurate with a radioactive silver nitrate ($^{110m}AgNO_3$). As these compounds are also inert to heat and light, they may be quite robust as security tags or shelf life indicators for time sensitive products (e.g., products with a shelf life of 6 to 9 months shelf life).

Ranges of Ingredients in the Antimicrobial Compositions and Devices

The amount of silver in the hydrogel compositions of the present disclosure may vary between 0.005% weight and 5.00% weight. However, in some embodiments, a range of 0.005%-2.5% weight may also be used. Further, in other embodiments, a range of 0.01%-0.50% weight may also be used. In this way, the amount of silver in the non-hydrogel antimicrobial compositions and devices ranges between 0.0001% weight and 5.00% weight. In still other embodiments, a range may be determined in parts per million (or ppm) based on a composition. Thus, in a non-hydrogel, the amount of silver in a silver cyanurate active agent may be between 10 and 5500 ppm based on a weight of the antimicrobial composition. Moreover, a different range may be used based on the type of application. Thus, in a hydrogel, the amount of silver in the hydrogel may be between 50 and 1000 ppm based on a weight of the hydrogel.

The amount of thickener in the said antimicrobial hydrogel compositions may vary between 0.10% weight and 10.00% weight, though the range 0.25%-7.50% weight may also be used. If two thickeners are employed, the weight ratio of one thickener to the second thickener may vary from about 1:20 to about 20:1 with total thickener content restricted by the above range. The humectant concentration of said antimicrobial hydrogel compositions may vary between 1.00% weight and 40.00% weight though the range 5.00%-20.00% weight may also be used. If two humectants are used, their weight ratio similarly may vary from about 1:20 to 20:1. The total additives content (including colorant, skin enhancing agents etc.) of said antimicrobial hydrogel compositions may vary between 0.0001% weight and 5.00% weight. The minimum amount of water in said antimicrobial hydrogel compositions is 40.00% weight and is adjusted once the concentrations of other ingredients are fixed. This minimum amount of water does not apply to other non-hydrogel antimicrobial compositions such as suspensions, o/w emulsions, w/o emulsions or emulgels, pastes, oily suspensions or liquids or other non-aqueous amorphous compositions. The amount of silver in the antimicrobial devices of the present disclosure may vary between 0.0001% weight and 10.00% weight based on the weight of the device.

Test Methods

Various test methods were attempted to evaluate the robustness of the antimicrobial compositions and devices of the present disclosure.

Light Exposure Testing
  (a) Table lamp light exposure test (TLE)
    The samples of the said compositions contained in either glass vials or 15 ml PP tubes (BD Falcon) were placed under a table lamp (turned on) at a distance of 12 to 15 inches for continuous exposure. The incandescent lamp wattage was 60 W. After the desired duration of exposure, the test samples were examined for visible discoloration by holding it against a white plain paper. Non-hydrogel samples were examined against the control samples protected from light.
  (b) Sun light exposure test (SLE)
    The samples of the test compositions were contained in either glass vials or 15 ml PP tubes and exposed to direct sunlight. The exposure was carried out during the hours of 9:00 am and 3:00 pm., and the exposure testing took place over the calendar year. The intensity of sunlight corresponded to the sunlight experienced at 45N latitude.

Thermal Testing
  (a) Accelerated age test
    To assess the prototype hydrogel compositions for shelf life, samples were placed in 15 ml PP tubes or were contained in commercial PE or PP tubing and placed in an oven set to 55 C. The samples were visually examined qualitatively for discoloration or physical changes such as loss of viscosity and syneresis.
  (b) Steam sterilization
    One steam sterilization cycle was imposed on gel prototypes to evaluate their ability to withstand elevated temperatures. The gel samples contained in 15 ml or 50 ml PP tubes or other non-hydrogel prototypes (in sealed foil pouches) were examined post sterilization for any adverse temperature effect on its color, viscosity, texture, phase separation etc.

Microbiological Testing

The antimicrobial activity of the hydrogel compositions and various device prototypes comprising silver cyanurate compounds was verified by standard zone of inhibition assay known to those skilled in the art. Briefly, in this assay, samples were placed on plates with proprietary agar formula (similar to Mueller Hinton Agar (MHA)) that were inoculated with bacteria and incubated at 37 C overnight. If antimicrobial activity in the sample was present, it formed a clear zone around the edges. As negative control, the samples without the silver active compound were used. In some tests, positive control was provided by use of commercial product samples with silver active compounds, e.g. Silvasorb®, Normlgel® Ag, SilverSept® gel or Maxorb® Ag. Primarily two microorganisms, one a gram positive bacteria Staphylococcus aureus ATCC6538 and the other gram negative Pseudomonas aeruginosa ATCC9027 were employed in the assay. To examine broad spectrum antimicrobial activity, various different types of organisms including MRSA and VRE were obtained. In investigating the broad spectrum activity, the ZOI assay was performed slightly differently. Instead of laying the samples on plates individually inoculated with different types of bacteria, the bacterial inoculums were streaked as parallel lines on one plate. After streaking the inoculum linearly, the samples were deposited as a continuous bead string in perpendicular direction to the streak lines. Evidence of antimicrobial activity in the sample was seen in the form of interruptions on both sides of the edges of the sample string.

A bacterial challenge assay was employed to verify antimicrobial activity of liquid compositions (suspensions) of the silver cyanurate compounds. Briefly, to the aliquots of the liquid compositions, bacterial inoculums were added and the samples were incubated at 37 C overnight. Thereafter, the test samples with silver were treated with sodium thioglycolate solution to neutralize silver and plated on agar plates (note if the samples contained less than 75 ppm silver, the use of sodium thioglycolate was omitted). As a control, the inoculum was added to liquid aliquot without silver and incubated at 37 C as above. Next day, the control sample was plated on agar plates and again incubated at 37 C for 24 h to 48 h to let the bacterial colonies grow and become visible. From the bacterial count of the control sample and the count of surviving colonies of the test samples, the log reduction, a quantitative measure of the antimicrobial activity was calculated.

Sterilization

A majority of the hydrogel prototypes of the present disclosure were tested for their ability to withstand elevated temperatures simply by subjecting them to one steam sterilization cycle. The test samples experienced temperature rises from 20 C to 122 C over 15 min, followed by constant temperature of 122 C for 15 min and finally a cool down from 122 C to ~40 C over 3 h. Thus, the test samples experienced nearly 3.5 h of hostile temperature condition.

Physical Properties

For a thixotropic material, viscosity is not a good measure of the characteristic yield stress that is overcome before it begins to flow. The yield stress was determined on a rheometer such as a cone and plate or parallel plate type by conducting strain and frequency sweeps. This technique is known to those ordinarily skilled in the art of physical properties characterization. For measuring traditional viscosity, a concentric cylinder viscometer (with variable spindle set) such as Brookfield viscometer (Model LVDVE115) was employed.

DEFINITIONS

In the following paragraph, various terms are defined in the context of the present disclosure;

"Low level" of silver means a silver content <1000 ppm by weight

"Moderate level" of silver means a silver content between 1000 ppm and 2000 ppm by weight "High level" of silver means a silver content >2000 ppm by weight "Sunlight resistant" or "light stable" or "inert to light" is defined as having no visible sign of discoloration (color change following exposure that will add shade of black, brown, yellow or purple) following one of two exposures: (i) 30 days continuously under a 60 W incandescent table lamp (turned on) at a distance of 12"-15" or (ii) one hour of continuous sunlight exposure at 45N latitude.

"Steam sterilizable" or "heat stable" or "inert to heat" is defined as having no visible sign of discoloration (color change following exposure that will add shade of black, brown, yellow or purple) after one steam sterilization cycle (122 C for 15 min) that includes periods of warming up and final cool down to room temperature (<40 C).

The words "compounds" and "derivatives" in the context of silver cyanurates of the present disclosure mean the same unless the context clearly dictates otherwise.

It should be noted that as used in this specification and the appended claims, the singular forms "a", "an" and "the" include plural referents unless the context clearly dictates otherwise.

All patents, patent applications and references included herein are specifically incorporated by reference in their entireties.

It should be understood, of course, that the foregoing relates to exemplary embodiments of the present disclosure and that numerous modifications or alterations may be made therein without departing from the spirit and the scope of the disclosure as set forth in the disclosure.

Although the exemplary embodiments of the present disclosure are provided herein, the present disclosure is not limited to these embodiments. There are numerous modifications and alterations that may suggest themselves to those skilled in the art.

The present disclosure is further illustrated by the way of the examples contained herein, which are provided for clarity of understanding. The exemplary embodiments should not be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

ILLUSTRATIVE EXAMPLES

Example 1

Preparation of Mono- and Di-Sodium Cyanurate

To a 50 ml PP tube, deionized water (~23 ml) and pellets of solid sodium hydroxide (~0.0922 g, Sigma-Aldrich) were added. The tube was vortexed to dissolve the solids and yield a ~0.1M solution. Next, cyanuric acid powder (~0.297 g) was added to the tube corresponding to 1:1 molar ratio with respect to sodium hydroxide. The contents were vortexed and heated in a microwave oven to dissolve the acid powder to form sodium cyanurate. The contents were cooled to room temperature and then the tube transferred to a refrigerator. After 24 h, the tube was examined and was found to contain fine needles of sodium cyanurate hydrate ($NaH_2C_3N_3O_3.H_2O$) which is consistent with a published report (see Seifer G. B., Russian Journal of Coordination Chemistry, Vol. 28, No. 5, p 301-324 (2002)). The TGA scan confirmed the presence of one molecule of water of crystallization that was lost ~175 C. Element anal: theor: C, 21.30%; H, 2.37%; N, 24.85%; Na, 13.61%; actual: C, 21.26%; H, 2.51%; N, 24.51%; Na, 13.10%.

The di-sodium cyanurate was obtained as follows. To a 400 ml glass beaker with stir bar, cyanuric acid (2.58 g, 20 mmol), deionized water (30 ml) and sodium hydroxide solution (10 ml, 7.5M) were added and the contents heated to ~80 C to yield a clear solution and maintained at 80-85 C for 1 h. Periodically water was added to maintain the same liquid volume. After the heating for one hour, the liquid was cooled to room temperature. Very small amount of solids that were present were filtered off. A portion of the filtrate (10 ml) was transferred to a second glass beaker (~250 ml capacity) and heated to remove most of the water. Solids appeared when ~1-2 ml liquid was left in the beaker that was then cooled to room temperature. To the solids, aqueous ethanol (40 ml, 50% v/v) were added and the solids were recovered and dried (~0.42 g). The ethanolic filtrate was left in the refrigerator (~4 C) overnight to crystallize more needle like solids that were filtered and dried (~0.33 g). The TGA scan of di-sodium cyanurate showed it was present as monohydrate ($Na_2HC_3N_3O_3.H_2O$) with water loss at ~110 C. Element anal: theor: C, 18.84%; H, 1.57%; N, 21.98%; Na, 24.08%; actual: C, 18.89%; H, 1.58%; N, 21.66%; Na, 23.60%.

Example 2

Synthesis of Ammonium Cyanurate Compound

In a 100 ml glass Erlenmeyer flask, cyanuric acid (0.645 g, 5 mmol, Sigma Aldrich) and deionized water (10 ml) were added. Ammonium hydroxide solution (0.4 ml, 14.8M) was pipetted into the acid water mixture. The contents were heated in a microwave oven in several 15 s durations to obtain a clear solution. Within minutes when the hot solution was left to cool down, fine crystals began to appear. The flask was covered with Saran® wrap film and left ~4 C in a refrigerator overnight. Next day, the crystals were recovered by filtration, washed and dried at 45 C for several hours (0.47 g, yield ~64%). The TGA scan showed a loss of ammonia consistent (theor: 11.64%, actual: 11.96%) with published work. No water of hydration was associated with the compound.

Example 3

Preparation of Gel Containing Mixed Silver Cyanurate as Antimicrobial Active Compound The preparation of amorphous aqueous gel with mixed silver cyanurate derivative was carried out as follows. According to the published paper (by Seifer G. B. and Tarasova, Z. A., Zh. Neorg. Khim., Vol. 34, pp. 1840-43, 1989), addition of soluble silver salt solution to monosodium cyanurate solution in 1:1 mole ratio results in a variable composition which was broadly termed as mixed silver cyanurate.

The first step was to prepare stock monosodium cyanurate solution. To a 50 ml polypropylene conical bottom tube (BD Falcon), monosodium cyanurate hydrate (~0.169 g, 1 mmol) was added followed by ~10 ml deionized water. The tube was capped and the contents briefly vortexed. Then, the tube contents were heated carefully in a microwave oven (Panasonic 1200 W) while taking care that the contents did not boil over. The hot contents were vortexed to dissolve the salt to yield a clear solution comprising monosodium cyanurate (0.1M).

In a 100 ml polypropylene plastic cup, weighed quantities of Laponite XLG (~0.4 g, Southern Clay Products, Gonzales, Tex.), Hydroxyethyl cellulose (~0.1 g, Lotioncrafter Inc.) and Glycerol (~2.0 g, Lotioncrafter Inc.) were added and hand-mixed with a SS spatula to form a paste. In a second similar cup, deionized water (~15.5 ml) was heated to near boiling in a microwave oven. The hot water was poured into the first cup. Immediately thereafter, the paste was hand-mixed vigorously with a spatula to obtain a viscous clear gel that was left to cool to room temperature (~15 min).

Next, ~1.0 ml of the monosodium cyanurate solution made above (and kept warm at ~40 C to prevent salt from dropping out of solution) was added to the viscous gel and blended in to uniformity. Finally, under low lighting conditions ~1.0 ml aqueous silver nitrate solution (0.1M) was added to the gel in three aliquots; each time mixing in the aliquot before adding the subsequent portion. The gel became more opaque with each aliquot addition but was pleasing and smooth to feel.

A small portion (~3 to 4 g) was transferred to a dram vial and capped. The vial was left ~12" from the incandescent lamp (60 W) and continuously exposed to the light for 24 h. Another similar portion was transferred to a second dram vial. The vial was capped and placed in an oven set to ~55 C for a thermal stress test. The remaining gel was transferred to a 50 ml PP tube and kept protected from light at room temperature.

After 24 h, the light exposed gel sample was examined and showed no discoloration. It looked identical to the gel sample kept protected from the light. The thermally stressed gel sample when examined after 2 weeks at 55 C showed a trace of brown color compared to gel maintained at room temperature. The combined results suggested that the amorphous gel made possessed excellent resistance to discoloration induced by light and heat. In this way, the antimicrobial compound is included within an aqueous clear gel, and the aqueous clear gel with the silver cyanurate active agent is resistant to discoloration via light. Thereby, the clear gel maintains a transparent color in response to light exposure.

Example 4

Preparation of Gel with Mixed Silver Cyanurate Omitting Hydroxyethyl Cellulose as Thickener To a 100 ml glass beaker ~15.2 ml of deionized water were added followed by slow addition of ~0.8 g Laponite XLG powder to the water under stirring. Over the next 30 minutes, the stirred contents transformed to a clear gel. The beaker was tared and glycerol (~2.0 g) was added which caused the viscosity of the gel to briefly increase. The glycerol was stirred into the gel which did not seem to affect its clarity. Next, ~1.0 ml of warm 0.1M monosodium cyanurate solution was added and mixed into the gel to uniformity. The gel had gained a shade of opacity though it remained mostly clear. Finally, as before ~1.0 ml silver nitrate solution (0.1M) was added in roughly 3 equal aliquots to the gel. Upon completion of silver salt solution, we noticed slight increase in the opacity though it was much less than when hydroxyethyl cellulose was used as thickener in the example above. Over next few days we observed that the opacity decreased making the gel look practically clear. Though, the gel was thixotropic, it was practically transparent, smooth to feel and readily spreadable. The pH of the gel was ~7.

Despite its clarity, the gel sample showed no discoloration after 24 h continuous light exposure and in appearance was similar to the gel sample protected from light. This characteristic of the gel sample is quite remarkable considering most silver salt containing gels discolor upon continuous light exposure.

When tested for antimicrobial activity against *Staphylococcus aureus* ATCC 25923 and *Pseudomonas aeruginosa* ATCC 27853 in a zone of inhibition assay, the gel sample showed clear zones confirming its activity. The theoretical silver content of the gel was ~540 ppm so its antimicrobial activity was expected. In a daily serial transfer ZOI assay, the gel sample sustained strong antimicrobial activity for 3 days against a gram positive bacteria (*S. aureus* ATCC 6538), a gram negative bacteria (*P. aeruginosa* ATCC 9027) and a yeast (*C. Albicans* ATCC 10231).

The sample gels thixotropic characteristic of yield stress was determined using a rheometer (Rheometrics Scientific RFS Model II with 25 mm parallel plates) from the strain and frequency sweeps. The measured value of yield stress at ~25 C was 249 Pa.

Example 5

Comparative Example—Preparation of Gel Containing Silver Saccharinate by Method A A comparative gel sample was prepared similar to the gel in Example 4 (keeping its theoretical silver content substantially the same) except silver saccharinate was the active compound. Its resistance to discoloration by light was compared with the gel in Example 4.

The following ingredients were used: Glycerol (2.00 g), Laponite XLG (0.80 g), Saccharin (0.027 g, FW 183.2, corresponding to a slight excess over stoichiometry with respect to $AgNO_3$), silver nitrate (1.0 ml, 0.1M) and deionized (DI) water (16.2 g).

In a 100 ml glass beaker Laponite was dissolved in DI water to obtain clear gel as before. In a 15 ml PP tube, saccharin powder was transferred and then glycerol was added. The tube was heated in a microwave oven to dissolve saccharin. The resulting saccharin solution was dripped into the clear gel and blended into uniformity. Finally, silver nitrate solution wad added and blended into a slightly hazy gel.

A glass dram vial with a portion of the prepared gel exposed to table lamp light from a distance of 12" discolored to brown yellow color after 16 h. The gel sample protected from light also substantially completely discolored to brown yellow color indicating poor resistance to light induced discoloration (photo-reduction).

Example 6

Comparative Example—Preparation of Silver Saccharinate Containing Gel by Method B The gel in this example was prepared to compare its discoloration resistance with the gel in Example 4 (keeping the silver content same), but it was prepared by a different method than described in Example 5. A different method was attempted to examine if it had any effect on the discoloration resistance.

The gel was prepared in a 100 ml PP cup in a manner similar to that described in Example 4 except instead of monosodium cyanurate solution, ~1.0 ml of 0.1M sodium saccharinate solution was used.

A portion of gel in a glass dram vial discolored after 1 h upon light exposure and in that same time period the light protected sample also discolored. Both samples turned brown yellow indicating photo-reduction to silver nanoparticles. Thus, modifying the gel making procedure did not increase the discoloration resistance.

Example 7

Comparative Example—Preparation of Silver Chloride Containing Gel

The gel was prepared as comparative example to examine if the Laponite XLG based gel offered an environment to silver chloride as active compound to enhance its light discoloration resistance by possibly helping form small crystals of chloride salt which are known to be light insensitive.

The gel was made by the same procedure described for the gel in Example 4 except instead of monosodium cyanurate solution, 0.2M sodium chloride solution was employed. The resulting gel was somewhat less viscous than the gel in Example 4 and more opaque white but smooth and pleasant looking. The pH of the gel was ~7.

However, upon light exposure it discolored within 2 h to a purplish black color though the sample protected from light remained unchanged from its original opaque white.

Example 8

Comparative Example—Preparation of Silver Phosphate Containing Gel

The gel was prepared as in the Example 4 except instead of sodium cyanurate solution, mono sodium phosphate solution (0.1M) was used. The rationale was to see if a silver salt of tri-functional acid such as phosphoric acid (cyanuric acid is also a tri-functional acid) affords greater light discoloration resistance in the gel environment.

But, the results of the light exposed gel sample showed that the sample discolored to grey black color after 2 h. The light protected sample gave a hint of discoloration (the bright yellow shade of the gel sample had just turned a bit dull). Overall the gel imparted a faint yellow opacity and was smooth to feel. The pH of the gel sample was between 7 and 8.

Example 9

Preparation of Mixed Silver Cyanurate Containing Gel with a Different Formula

The following ingredients were used to prepare ~20 g gel. The ingredients and their amounts in parentheses are listed here: Glycerol (2.00 g), Laponite XLG (0.40 g), Sodium carboxymethyl cellulose (0.1 g, Ashland Chemical Natrasol® Grade 9H4F), monosodium cyanurate solution (1.0 ml, 0.1M), silver nitrate (1.0 ml, 0.1M) and deionized (DI) water (15.5 g).

In a 100 PP cup, the solids above were blended with glycerol. DI water was heated to 80 C in another cup and poured into the slurry and hand-mixed as the contents cooled to room temperature. Then monosodium cyanurate solution was added and again hand-mixed in. Finally, silver nitrate solution was added to obtain a smooth slightly opaque white viscous gel with silver content ~540 ppm.

Both samples of the gel (light exposed for 24 h and the light protected) showed no discernable difference suggesting no influence of light on the samples and both remained substantially unchanged from the time it was made, showing superior light discoloration resistance. With time, the gel sample seemed to show increased opacity but no discoloration. For a silver content of >500 ppm in an aqueous gel and not having any hint of discoloration by light is quite extraordinary.

Example 10

Gel Sample Containing Mixed Silver Cyanurate with Different Proportions of Thickeners A gel sample with silver content ~540 ppm was prepared by the same procedure disclosed in the Example 9 except the following amounts were used: Glycerol (2.00 g), Laponite XLG (0.32 g), Sodium carboxymethyl cellulose (0.08 g, Ashland Chemical Natrasol® Grade 9H4F), monosodium cyanurate solution (1.0 ml, 0.1M), silver nitrate (1.0 ml, 0.1M) and deionized (DI) water (15.6 g).

The gel was opaque white but smooth and could be spread easily. Both samples (24 h light exposed and light protected) showed no sign of discoloration when examined nearly a month later demonstrating superior light discoloration resistance.

Example 11

Gel Sample Containing Mixed Silver Cyanurate with Silver Content ~3000 ppm

Using the following ingredients and their listed proportions, the gel was made as follows: Glycerol (2.00 g), Laponite XLG (0.80 g), monosodium cyanurate solution (5.0 ml, 0.1M), silver nitrate (5.0 ml, 0.1M) and deionized (DI) water (5.3 g).

In a 100 ml PP cup, glycerol and Laponite were mixed into a paste. In a $2^{nd}$ cup, DI water and warm monosodium cyanurate solution were mixed and poured all at once into the paste. The contents began to thicken to a gel and were hand-mixed to uniformity with a spatula. Next, silver nitrate solution was added, 0.5 ml aliquots at a time until all additions were made (Note in this test, the lab lights were turned off during silver nitrate addition step as a precaution). With each aliquot of silver nitrate, the opacity increased. An opaque white, smooth to feel and pleasant gel was obtained though it was somewhat less viscous than the gel in Example 4.

The 24 h light exposed gel sample in appearance was similar to light protected sample indicating superior light discoloration resistance. Even after nearly a month, there was no discoloration of the light exposed sample though some syneresis of the gel was seen.

Example 12

Preparation of Gel Containing Mixed Silver Cyanurate with Color for Aesthetic Purposes A gel sample was made similar to the sample in Example 4 with an added feature of blue color to enhance its aesthetic appeal. The blue color was developed by employing a copper-glutamate complex. A collateral benefit of using copper complex was it was likely to also increase the antifungal activity of the gel via synergistic effect though with targeted silver content of ~540 ppm it was already lethal to fungi.

The copper-glutamate complex solution was prepared prior to the gel formulation step. Briefly, mono sodium glutamate (~0.169 g, Ajinomoto brand obtained from a local ethnic food store) was dissolved in 10 ml deionized water. In a second PP tube, ~0.249 g copper sulfate pentahydrate was dissolved in 10 ml DI water to obtain a bluish solution. The two solutions were combined to yield a clear navy blue shade solution that was maintained at room temperature until ready for use.

The following ingredients were blended in by the procedure in Example 4 in the proportions indicated: Glycerol (2.00 g), Laponite XLG (0.80 g), monosodium cyanurate solution (1.0 ml, 0.1M), silver nitrate (1.0 ml, 0.1M) and deionized (DI) water (14.8 g) and copper-glutamate complex solution (0.4 ml).

As before the silver cyanurate containing gel was prepared. In the final step, copper-glutamate complex solution was added that imparted a faint ice blue pleasing color to the gel. Qualitatively, the gel appeared similar to previously made gel samples containing Laponite XLG and mixed silver cyanurate with respect to viscosity but appeared to be more transparent. Over time it appeared that the gel sample had turned even more transparent. The pH of the gel was measured ~7.

The 24 h light exposed gel samples were unaffected by continuous light exposure and appeared substantially identical to the light protected sample suggesting no deleterious effect of copper-glutamate complex. The light protected gel sample, in a daily serial transfer ZOI assay, sustained strong antimicrobial activity for 3 days against a gram positive bacteria (*S. aureus* ATCC 6538), a gram negative bacteria (*P. aeruginosa* ATCC 9027) and a yeast (*C. Albicans* ATCC 10231).

The measured value of yield stress (at ~25 C) of the gel sample was 251 Pa.

Example 13

Effect of Sunlight on the Gel Samples Applied Topically to the Skin of a Human Subject The light exposed gel samples from Example 4 and the light protected gel sample from Example 12 were applied (approx. 100 mg each) topically as thin layer on the backside of the palm of hand of a human subject and exposed directly to afternoon sunlight continuously for 15 min. and then the applied area was examined. No staining of the skin area was seen which was quite remarkable. The subject also did not experience irritation consistent with the neutrality of the gel pH, which was around ~7.

Example 14

Preparation of Sodium Silver Cyanurate Ligand Complex Containing Gel in Large Quantity and with Excess of Monosodium Cyanurate By pro-rating the quantities of ingredients in the Example 12, the gel on 1000 g scale was prepared with one exception. That is the monosodium cyanurate solution amount was 20% excess over 1:1 mole ratio of cyanurate and silver nitrate with resulting reduction in the amount of DI water. Due to the use of an excess of cyanurate anion over silver cation, the ratio >1 was maintained. Under such situation, mixed silver cyanurate was formed. A lab stirrer/2 liter container assembly was used to accommodate the larger proportions. The finished gel was substantially identical to that made in the Example 12 with silver content ~540 ppm. The difference being an increased opacity compared to the gel in Example 12.

Example 15

Preparation of Mixed Silver Cyanurate and Copper-Glutamate Containing Gels with Varying Silver Contents Two gel samples were prepared in a manner identical to that in Example 12 except the amounts of monosodium cyanurate, silver nitrate and copper-glutamate complex solutions were altered to reflect the desired silver and copper contents of the finished gel samples.

One gel had theoretical target values of silver and copper as ~110 ppm and ~30 ppm, respectively. The second gel sample had silver and copper target values of ~220 ppm and ~60 ppm, respectively.

In appearance, these gel samples were practically transparent, very pleasing to the eyes, smooth and readily spreadable. None of the two were adversely affected by ambient office light when examined after several days on the bench, thus affirming their superior light discoloration resistance.

These gel samples with lower content of silver and copper are more suitable for treating minor cuts and wounds in the OTC market segment.

Example 16

Preparation of Alginate Fiber Based Non-Woven Dressing with Mixed Silver Cyanurate The previous examples demonstrated the superior light discoloration resistance of mixed silver cyanurate containing gels. To examine if the same resistance was extendable to other substrates, an alginate based non-woven dressing was treated to render it antimicrobial with mixed silver cyanurate.

In a 15 ml PP tube, ~11.6 ml 95% ethanol was pipetted followed by ~0.2 ml of warm clear 0.1M monosodium cyanurate and ~0.2 ml 0.1M silver nitrate solutions. This resulted in a fine mixed silver cyanurate suspension that was vortexed several times to keep the fine solids evenly dispersed.

In separate petri dishes (4" dia, BD Falcon), two ~2"×2" pieces of alginate non-woven dressing (from a source in PRC) were dripped with equal portions of the mixed silver cyanurate suspension in ethanol to evenly soak them. Each piece was drained off excess ethanol by holding it at one corner with a tweezer and the pieces were transferred to a nylon mesh and left in an oven to dry for 1 h. One dry sample was left under the table lamp for 24 h continuous light exposure and the other piece was protected from light.

After 24 h, the light exposed sample had discolored to a faint purplish gray color compared to the light protected sample, but the color change was not splotchy but uniform. Based on theory, the amount of silver in the alginate non-woven dressing post treatment on dry basis was ~3500 ppm. A commercial non-woven alginate dressing (Maxorb® Ag) exhibited comparable levels of light induced discoloration. Considering that the amount of silver is so high the limited discoloration suggested the mixed silver cyanurate possesses intrinsic light discoloration resistance uncommon to anti-microbial active silver compounds.

Example 17

Preparation of Mixed Silver Cyanurate Gel with Propylene Glycol as Humectant

The gel was prepared in a manner identical to that in the Example 4 except propylene glycol was used in place of glycerol as humectant. The resulting gel appeared to be less viscous than the gel from Example 3. The gel was practically clear, smooth and readily spreadable. The gel pH was about 7.

Upon 24 h light exposure under a table lamp, the gel sample showed no sign of discoloration consistent with previous observation with the gel in Example 4. The result suggested that propylene glycol was also suitable as humectant and did not adversely affect the light discoloration resistance.

Example 18

Preparation of Antimicrobial Hydrogel with Mixed Silver Cyanurate on 3 Kilo Scale This example demonstrates that the gel preparation is scalable. To a large polypropylene beaker (5 liter capacity) 2330 ml of deionized water was added. A high shear mixer (3" diameter Cowles blade, IKA) was immersed into the water so that the blade was about 1" above the bottom. At a stirrer speed of 800 rpm, 120 g Laponite XLG (Rockwood Additives Company, South Gonzales, Tex.) was introduced quickly into the vortex of the stirred water through a paper cone to minimize dust cloud. The speed was increased to ~1100 rpm as the clay mineral dispersed and the mixture thickened. After 20 minutes stirring, a clear thixotropic gel was obtained. Under continued stirring, Glycerol USP (300 g, Lotioncrafter Inc. WA) was added to the gel that briefly thinned but the viscosity was restored within 10 minutes. A warm solution of monosodium cyanurate (150 ml, 0.1M) was dripped slowly into the thick gel and mixed in for 5 minutes. This caused further thickening of the gel that was counteracted by raising the stirrer speed to ~1600 rpm. Finally, under continued stirring and dim light conditions, freshly prepared silver nitrate solution (75 ml, 0.2M) was dripped into the gel followed by rinse water (75 ml) used to rinse beakers containing salt solutions. The silver salt solution was thoroughly mixed in for 30 minutes to ensure completion of reaction such as, for example, cation exchange. Due to viscosity buildup, the stirrer was stopped several times and the semi-solids were hand-mixed with an 8" long flat SS blade spatula to yield a smooth clear to hazy gel. After waiting overnight to ensure there was no gel syneresis, a portion of the gel was set aside for testing and the rest was packaged in 1.5 oz polypropylene tubes. The theoretical silver content of the gel was ~540 ppm.

Steam sterilization of the prepared gel was carried out as follows. About ~20 g gel was transferred to a 50 ml PP tube (BD Falcon) that was loosely capped and placed in an autoclave and subjected to steam sterilization (121-122 C for 15 minutes). The gel containing PP tube that now was slightly warped was removed from the cooled autoclave and examined. Except for a slight increase in its opacity, no discoloration of the gel mass was seen. In a subsequent test, the steam sterilized gel sample was found to be antimicrobial against *Staphylococcus aureus* ATCC 6538 for 3 days in a serial transfer ZOI assay. Such maintenance of antimicrobial activity in silver containing gel that experienced elevated temperatures is quite remarkable.

Example 19

Broad Spectrum Antimicrobial Activity Testing of Gel with Silver Content ~540 ppm The broad spectrum antimicrobial activity of the gel of Example 18 was tested against 13 different microorganisms in a ZOI assay. Briefly, streaks of bacterial cultures were laid on agar plates and perpendicular to the streaks, gel sample was applied over as continuous string. As negative control, gel without silver was used. A silver containing gel sold in the market, Normlgel®Ag (Ag~1100 ppm) served as positive control.

The test results are tabulated below.

Table for Ex. 19:
Broad spectrum test results on gel with mixed silver cyanurate using ZOI Assay

| | | Zone width (mm) | | |
| --- | --- | --- | --- | --- |
| S No. | Micro-organism | Gel sample Example 18 | Negative Control | Positive Control |
| 1 | *Bacillus subtilis* ATCC 11774 | 3 | 0 | 4 |
| 2 | *Klebsiella pneumoniae* ATCC 33495 | 3 | 0 | 2 |
| 3 | Methicillin resistant *Staphylococcus aureus* ATCC 33592 | 4 | 0 | 3 |
| 4 | *Enterococcus faecium* ATCC 700221 | 7 | 0 | 6 |
| 5 | *Enterococcus faecalis* ATCC 19433 | 3 | 0 | 2 |
| 6 | *Enterobacter cloacae* ATCC 13047 | 3 | 0 | 2 |
| 7 | *Proteus mirabilis* ATCC 12453 | 3 | 0 | 3 |
| 8 | *Candida parapsilosis* ATCC 22019 | 12.5 | 0 | 9 |
| 9 | *Serratia marcescens* ATCC 13880 | 3 | 0 | 3 |

-continued

Table for Ex. 19:
Broad spectrum test results on gel with mixed silver cyanurate using ZOI Assay

| | | Zone width (mm) | | |
|---|---|---|---|---|
| S No. | Micro-organism | Gel sample Example 18 | Negative Control | Positive Control |
| 10 | Acinetobacter baumanni ATCC BAA-1605 | 5 | 0 | 5 |
| 11 | Escherichia Coli ATCC 8739 | 3 | 0 | 2 |
| 12 | Listeria Monocytogenes ATCC 19115 | 6 | 0 | 4 |
| 13 | Streptococcus pyogenes ATCC 19615 | 10 | 0 | 10 |

Example 20

Preparation of Antimicrobial Hydrogel with Mixed Silver Cyanurate on 3 Kilo Scale and Silver Content ~470 ppm The gel was prepared using the same equipment and procedure of Example 4 except the ingredients and their amounts listed here were employed: Deionized water (2700 g), Laponite XLG (120 g), glycerol (300 g), monosodium cyanurate solution (150 ml, 0.1M) and silver nitrate solution (150 ml, 0.1M). The theoretical silver content of the gel was ~470 ppm.

The gel was transferred to a white plastic PP pail and stored at ambient temperature for 9 months with temperature fluctuating between ~4 C and 35 C. Each month the gel mass was examined for any changes. Other than minor syneresis, no physical changes (viscosity, clarity, color or growth of micro-organisms) were observed. In packaged tubes however, no syneresis was observed over the same duration.

Example 21

Preparation of Gel with Theoretical Silver Content ~440 ppm and the Ratio of Cyanurate to Silver Ions 1.2

The rationale was to see if the ratio when skewed in favor of anion cyanurate increases the light discoloration resistance. Due to the cyanurate ions to silver ions ratio >1.0, the majority active compound is mixed silver cyanurate. In a 100 ml PP beaker, deionized water (15.4 ml) was pipetted and a magnetic stir bar was placed. Weighed quantity (0.8 g) of Laponite XLG clay mineral was quickly added to the stirred water and the contents stirred for 10 minutes to hydrate the clay to yield a viscous gel. Thereafter, glycerol (2.0 g), monosodium cyanurate solution 0.1M, 1 ml) and silver nitrate solution (0.1 M, 0.8 ml) were added in succession, mixing the ingredient thoroughly after each addition to obtain a smooth but slightly hazy and pleasant gel. A small amount of gel (~2.0 g) was transferred to a 15 ml PP tube that was capped and placed in direct sunlight. When examined after 4 h when the test was stopped, the gel remained clear with no discoloration. In a follow up test, gel (~2.0 g) was taken in another 15 ml PP tube and steam sterilized at 121-122 C for 15 minutes and then cooled to room temperature. Despite exposure to elevated temperature that could be construed as extreme for a silver containing aqueous composition, the gel remained unchanged, that is showed no sign of discoloration or change in viscosity.

Example 22

Preparation of Gels with Various Silver Cyanurate Derivatives with Theoretical Silver Content ~540 ppm Gels were prepared with mono-silver cyanurate and di-silver cyanurate as antimicrobial actives. Their suspensions were made by maintaining appropriate mole ratio of corresponding sodium cyanurate to silver nitrate that were then dripped into the base gel. By reversing the order of addition, additional gels were prepared with mixed silver cyanurate compounds obtained in situ by adding silver nitrate solution into base gel containing mono-, di-sodium cyanurate respectively in 1:1 mole ratio. The base gel comprised of glycerol, Laponite XLG and deionized water. In finished gel formulations, the weight percent of glycerol, Laponite XLG and silver were ~10%, ~4% and ~0.054% respectively.

All gel samples were either transparent or hazy but smooth, thixotropic and easy to spread. The pH of all gels was between 7 and 8 units. The gels did not discolor even after continuous table lamp light exposure for 1 week. When steam sterilized, of the four gel samples only di-silver cyanurate containing gel showed discoloration. Separately, when small gel samples in PP tubes were exposed to direct sunlight, only the di-silver cyanurate comprising gel showed hint of grey 1.5 h respectively. Still, the discoloration resistance was observed to be quite strong. The remaining three gel samples showed no evidence of discoloration through 2.5 h when the exposure was discontinued.

Example 23

Comparison of Performance of Gels Made with Silver Cyanurate Derivatives and Various Silver Salts with Respect to Light Exposure On 20 g scale, gel samples were prepared by mixing appropriate amounts of glycerol, Laponite XLG clay and water. Finally, silver salts were formed in-situ by blending corresponding sodium salt solutions (0.1M) which was followed by silver nitrate solution (0.1M). Note in all gel preparations, silver nitrate was added under dark. The finished gels contained glycerol, clay and silver at 10%, 4% and 0.054% weight, respectively. The finished gel samples were observed for discoloration or lack thereof when made fresh, at 24 h and after either 1 week or 30 days after being continuously exposed to a 60 W table lamp at a distance of 1 to 1.5 feet. The results are summarized in the table below.

The results showed that of the 22 silver salts tested, silver sulfadiazine and the two silver cyanurate derivatives in the gel did not show discoloration at 24 h. But after 1 week exposure, the gel with silver sulfadiazine showed a hint of discoloration. Thereby, the gels comprising the silver compounds comprising s-triazine ring showed exceptional resistance to discoloration by light as evidenced by no color change after 4 weeks of light exposure.

Example 24

Preparation of Gel with Urea as Humectant

As before, urea (2.0 g), Laponite XLG (0.8 g) and deionized water (15.2 ml) were mixed to obtain the base gel. To this, warm monosodium cyanurate solution (1.0 ml, 0.1M) was added followed by silver nitrate solution (1.0 ml, 0.1M) in the dark. After blending the contents thoroughly, a transparent to hazy gel was obtained. When exposed to direct sunlight for 3 h the gel showed no hint of discoloration which is quite remarkable. No discoloration of the gel was seen after steam sterilization.

Table for Ex. 23
Light Exposure Test Data on Gels with Different Silver Compounds

| Silver Compound | Gel color after continuous light exposure | | |
|---|---|---|---|
| | Fresh | After 24 h | After 30 days |
| Silver Chloride | Purplish black after 2 h | Dark Purplish black | Not tested |
| Silver Carbonate | Hint of brown after 10 min | Brown black | Not tested |
| Silver Phosphate | Grey black after 2 h | Grey black | Not tested |
| Silver Saccharinate | Yellow brown | Dark amber brown | Not tested |
| Silver Acetyl Salicylate | Hint of grey | Brown black | Not tested |
| Silver Mono-tartrate | Hazy gel | Brown black | Not tested |
| Silver Mono-maleate | Smooth hazy gel | Brown yellow | Not tested |
| Silver Lactate | Brown during preparation | Not tested | Not tested |
| Silver Salicylate | Brown after 0.5 h | Not tested | Not tested |
| Silver Propionate | Hint of brown after 10 min | Brown black | Not tested |
| Silver Sulfo-succinate | Brown after 0.5 h | Brown black | Not tested |
| Silver Benzene sulfonate | Brown after 0.5 h | Brown black | Not tested |
| Silver Mono-succinate | Trace of yellow grey | Brown black | Not tested |
| Silver Gluconate | Light yellow after 10 min | Brown black | Not tested |
| Silver Sorbate | Hint of yellow grey after 1.5 h | Brown black | Not tested |
| Silver Oleate | Opaque white; turned dull yellow after 1 h | Light yellow brown | Not tested |
| Silver Glycolate | Hint of brown grey | Brown grey | Not tested |
| Silver Benzoate | Light brown after 10 min | Brown black | Not tested |
| Silver Sulfadiazine | Opaque white | Hint of grey | Slightly more grey |
| Silver Itaconate | Hint of yellow brown | Brown black | Not tested |
| $C_3N_3H_2O_3Ag$ | Hint of haze but transparent | No change, nearly transparent | No change, nearly transparent |
| $C_3N_3O_3HAg_2$ | Hint of haze but transparent | No change, nearly transparent | No change, nearly transparent |
| $Na[Ag(C_3N_3O_3H_2)_2]$ | Hint of haze but transparent | No change, nearly transparent | No change, nearly transparent |
| $NaAgHC_3N_3O_3$ | Hint of haze but transparent | No change, nearly transparent | No change, nearly transparent |

Example 25

Thermal Stability of Gels Containing Silver Cyanurate Derivatives and Silver Sulfadiazine Gels with mixed silver cyanurate and sodium silver cyanurate ligand complex were prepared by the method described in Example 4. With silver sulfadiazine, the micronized powder corresponding to ~540 ppm silver was added into the gel. The gel samples were exposed to elevated temperatures by subjecting them to steam sterilization. The theoretical amount of silver in the gels was varied. The results are tabulated below. As described herein, the aqueous clear gels with silver cyanurate are further resistant to discoloration via heat.

Table for Ex. 25:
Observations of hydrogels with silver cyanurate compounds after steam sterilization

| Theor. Silver content (ppm) | Ratio of cyanurate/silver ions | Active compound | Color before steam sterilization | Color after steam sterilization |
|---|---|---|---|---|
| 540 | 1 | Mixed silver cyanurate | Hazy | No discoloration |
| 2700 | 1 | Mixed silver cyanurate | Opaque white | No discoloration |
| 440 | 1.25 | Mixed silver cyanurate | Hazy to clear | No discoloration |
| 220 | 2.5 | Sodium silver cyanurate ligand complex | Hazy to clear | No discoloration |
| 110 | 5 | Sodium silver cyanurate ligand complex | Hazy to clear | No discoloration |

Table for Ex. 25:
Observations of hydrogels with silver cyanurate compounds after steam sterilization

| Theor. Silver content (ppm) | Ratio of cyanurate/silver ions | Active compound | Color before steam sterilization | Color after steam sterilization |
| --- | --- | --- | --- | --- |
| 540 | NA | Silver sulfadiazine | Opaque white | Discolored to brown |

Example 26

Preparation of Talc Powder Impregnated with Silver Cyanurate Derivative (Ag ~1000 ppm)

This example demonstrates that antimicrobial property can be easily imparted to an inorganic solid support matrix which then can be blended into variety of other solid articles such as catheters, plugs etc. or can be made into coatings for surface application.

Unscented talc powder (2.5 g) was transferred to a plastic beaker (150 ml capacity) with stir bar. Ethanol (5 ml) was poured over to wet the powder and then deionized water (30 ml) was further added. Under stirring and dark conditions, warm monosodium cyanurate solution (0.5 ml, 0.1M) was added and immediately followed by silver nitrate solution (0.45 ml, 0.1M) to precipitate out a mixture of mixed sodium silver cynaurate ligand and variable composition silver cyanurate in the presence of talc. The contents were stirred for 1 h in the dark. Thereafter, the talc suspension was centrifuged. The supernatant was discarded, fresh ethanol (45 ml) was added. The contents vortexed to re-suspend the solids and then re-centrifuged. The liquid over the solids was discarded and fresh ethanol was added and the contents vortexed again and then filtered and the solids dried in an oven at 45 C for 2-3 h. A portion of silver impregnated talc powder in a petri-dish was exposed to table lamp light continuously for 60 days. No change in color was seen between exposed and light protected talc powder. The silver impregnated talc can be used to absorb excessive moisture due to sweat from the feet and also can be used for relief from and the eradication of fungi responsible for athlete's foot. In place of talc, one can also use zinc oxide powder or titanium oxide powder and a variety of other inorganic supports to produce antimicrobial powders for both medical and industrial applications. In this way, the antimicrobial compound may be further included within a solid substrate, wherein the solid substrate is selected from the group consisting of talc powder, zinc oxide power, and titanium oxide powder. The antimicrobial function may also be imparted to articles, objects or surfaces by, for example, vacuum deposition of the silver cyanurate derivatives either singly or as a mixture. In this way, the methods are not limited to traditional preparation methods but also include methods like vacuum deposition.

Example 27

Preparation of Mixed Sodium Silver Cyanurate Ligand Complex Impregnated Fibrous Substrates In this illustrative example, we demonstrated the impregnation of absorbent paper (Bounty® brand) and cotton gauze (J&J) with antimicrobial silver cyanurate derivative at theoretical silver loading of ~1400 ppm and ~500 ppm, respectively. As described, the antimicrobial silver cyanurate compounds may be embedded within a wound dressing, a cotton gauze, and/or an absorbent paper.

First the silver containing suspension was prepared as follows. In a 50 ml PP tube, mono sodium cyanurate solution (5 ml, 0.1M) and silver nitrate solution (1 ml, 0.1M) were added in that order to produce a fluffy white precipitate that was broken down by vortex mixing the tube contents. After that, dilute ammonium hydroxide (25 ml, 0.3M) was added and the contents vortexed again. To a 4"×4" piece of paper, 4 ml of the suspension was applied with a pipette and the piece was transferred to a nylon mesh support and dried in an oven at 45 C for 1 h. A 2"×2" cotton gauze was weighed and then placed in a petri-dish. An aliquot of the suspension substantially equal to its weight was applied to the cotton gauze which was then transferred to another nylon mesh and dried at 45 C for 1 h.

The silver impregnated paper and gauze samples were cut in half; one part was saved protected from light and the remaining was continuously exposed to table lamp light for a period of 45 days during which it was monitored for discoloration. No discoloration of paper or the gauze whatsoever was observed. Separately, silver impregnated paper piece was exposed to direct sunlight for 6 h without any discernable discoloration. The exposed samples in ZOI assay were found antimicrobial and were effective against *Staphylococcus aureus* ATCC6538 and *Pseudomonas aeruginosa* ATCC9027. Such robust discoloration resistance against light have not been observed in the past for any silver containing products. When steam sterilized in foil pouches, silver containing samples of paper and cotton gauze were practically unchanged in appearance when compared to corresponding non-steam sterilized samples.

Example 28

Preparation of Silver Impregnated Water Glass Coating

This example illustrates the preparation of coating made of sodium silicate embedded with mixed silver cyanurate. To a 15 ml PP tube, deionized water (0.5 ml), sodium cyanurate solution (0.11 ml, 0.1M) and silver nitrate solution (0.11 ml, 0.033M) were added in that order to yield a fluffy white precipitate of mixed silver cyanurate. The tube contents were vortexed to produce a uniform suspension. In a second PP tube, ~1 g of 40% aqueous sodium silicate solution (Raku Gold Pottery Co.) was transferred. To the silicate solution, all of the mixed silver cyanurate suspension was added and vortexed to uniformity to yield a pearlescent viscous solution.

A wet coating of the viscous solution was formed on a clean glass slide (1"×4", Fisher Scientific). The slide was placed in an oven at ~80-100 C for 1 h to cure the coating embedded with silver. A hazy hard coating with several fissures (small and large) was obtained. The slide with coating was left under the table lamp for continuous light exposure. After 60 days exposure no visible discoloration was observed. Thereafter the coated slide was tested against *Staphylococcus aureus* ATCC6538 for antimicrobial activity by ZOI assay. It showed clear inhibition zones indicating positive antimicrobial activity.

Example 29

Preparation of Gel with Silver Nitrate-Melamine Complex with Silver Content-540 ppm In a 100 ml PP cup, the following ingredients and solutions were mixed: glycerol (2 g), Laponite XLG (0.8 g), deionized water (15.2 g), melamine (1 ml, 0.1M), silver nitrate (1 ml, 0.1M) to produce a smooth slightly hazy thixotropic gel. Exposure to direct sunlight for 4 h did not produce any discoloration of the gel, though steam sterilization turned the gel brown black. The gel was antimicrobial in ZOI assay.

Example 30

Preparation of Gel Sheet Material Containing Mixed Silver Cyanurate and Sodium Alginate As a first step, thixotropic gel (20 g) containing mixed silver cyanurate was prepared following the method of Example 21 having theoretical silver content 440 ppm. In the second step, in a PP cup, sodium alginate (0.2 g, Sigma Aldrich) was dissolved in 10 ml hot deionized water and hand-mixed to a viscous semi-solid gel. To the resulting sodium alginate solution, 4 g of gel with silver was added and thoroughly mixed to uniformity. About ~7 g of the resulting mixture was poured into a ~2" dia plastic petri-dish and left to dry at room temperature over 2-3 days. A round flexible gel sheet piece weighing ~2 g was removed from the petri-dish; half of which was left exposed to office light for 120 days and the other half was sealed in a foil pouch and autoclaved. The light exposed piece did not undergo any change in color over four months, but the autoclaved piece turned uniformly orange brown. The gel sheet could suitably be used as antimicrobial dressing. The theoretical silver content of gel sheet was calculated ~800 ppm.

Example 31

Impregnation of Pre-Made Gel Sheet with Monosilver Cyanurate Compound

A piece of pre-made gel sheet (prepared according to the U.S. Pat. No. 5,196,190) weighing ~0.5 g was placed in a petri-dish. A solution made by mixing silver nitrate (0.1 ml, 0.1M), deionized water (1.0 ml) and dilute ammonium hydroxide (1.0 ml, 0.3M) was spread evenly over the piece to hydrate it for 30 min. Next, cyanuric acid solution (1.0 ml, 0.3M) was spread of the same piece to soak up the acid. The piece was left protected from light for 1-2 h at room temperature. The resulting piece imparted a faint opaque white color. The piece was found to be antimicrobial against *Staphylococcus aureus* ATCC3528 for 3 days in a serial transfer ZOI assay.

Example 32

Preparation of Gels with Various Silver Cyanurate Derivatives as Actives at Silver Content of 540 ppm Each sample gel was prepared on 20 g scale. First, monosodium and disodium salts of cyanuric acid were prepared as described in Example 1 and then their 0.1M solutions were prepared. Next, the base gels were made by hydrating LaponiteXLG (0.8 g) in deionized water (15.2 ml) followed by glycerol addition (2.0 g). Finally the gels with active compound were made by adding silver nitrate solution and the cyanurate in the order described.

(a) For monosilver cyanurate active, monosodium cyanurate (1.0 ml, 0.1M) was added to silver nitrate (1.0 ml, 0.1M) in a separate PP tube to produce a white suspension that was then blended into the base gel uniformly to produce a smooth opaque white gel.

(b) For mixed silver cyanurate active, monosodium cyanurate (1.0 ml, 0.1M) was directly added to the base gel, blended in uniformly followed by silver nitrate (1.0 ml, 0.1M) and mixed to uniformity to obtain a hazy to transparent gel.

(c) For sodium silver cyanurate ligand complex as active, monosodium cyanurate (1.0 ml, 0.1M) was directly added to the base gel, blended in uniformly followed by silver nitrate (0.5 ml, 0.1M) and make up deionized water and mixed to uniformity to obtain a hazy to transparent gel.

(d) For di-silver cyanurate active, disodium cyanurate (0.5 ml, 0.1M), deionized water (0.5 ml) was added to silver nitrate (1.0 ml, 0.1M) in a separate PP tube to produce a white suspension that was then blended into the base gel uniformly to produce a smooth faint opaque white gel.

(e) For mixed sodium silver cyanurate salt active, disodium cyanurate (1.0 ml, 0.1M) was directly added to the base gel, blended in uniformly followed by silver nitrate (1.0 ml, 0.1M) and further mixed to uniformity to obtain a hazy to transparent gel.

Each of the gel samples was continuously exposed to table lamp light for 1 week. No discoloration was observed. Separate samples under SLE test showed no discoloration for exposure up to 2.5 h except the sample gel (d) above which discolored after 1.5 h, In ZOI assay employing *Staphylococcus aureus* ATCC3528 and *Pseudomonas aeruginosa* ATCC9027, each gel exhibited antimicrobial activity. Furthermore, none of the gel samples above showed discoloration after steam sterilization and thus showed excellent thermal stability.

Example 33

Thermal Stability of Suspensions of Various Silver Cyanurate Derivatives

Because of the strong oxidizing nature of silver ions, they tend to photo-reduce very rapidly to elemental silver (and imparting grey, brown or black color), more so in aqueous environments. Hence, silver containing products that contain water are very susceptible to discoloration both by heat and light. Whether the silver cyanurates derivatives in aqueous environments behave, that is discolor like an overwhelming majority of silver compounds, was investigated in this test. In addition, the steam sterilized aqueous compositions comprising silver cyanurate derivatives were further examined to see if they retained their antimicrobial properties. For the test, each suspension (with specific cyanurate derivative) was prepared under dark light in separate PP tubes (15 ml, BD Falcon) as follows:
  (i) Added monosodium cyanurate (1.0 ml, 0.1M) to silver nitrate (1.0 ml, 0.1M) and vortexed for 1-2 minutes for mono-silver cyanurate derivative
  (ii) Added silver nitrate (1.0 ml, 0.1M) to monosodium cyanurate (1.0 ml, 0.1M) and vortexed for 1-2 minutes for mixed silver cyanurate derivative
  (iii) Added disodium cyanurate (0.5 ml, 0.1M), deionized water (0.5 ml) to silver nitrate (1.0 ml, 0.1 M) and vortexed for 1-2 minutes for di-silver cyanurate derivative
  (iv) Added silver nitrate (1.0 ml, 0.1M) to disodium cyanurate (1.0 ml, 0.1M) and vortexed for 1-2 minutes for mixed sodium silver cyanurate derivative $Ag_2C_3N_3HO_3 \cdot H_2O$: theor: Ag, 59.8%; C, 9.98%; N, 11.64%; H, 0.83%; actual: Ag, 59.17%; C, 10.82%; N, 12.48%; H, 0.56%.
$NaAgC_3N_3HO_3 \cdot H_2O$: theor: Ag, 39.1%; Na, 8.34%; C, 13.05%; N, 15.22%; H, 1.09%; actual: Ag, 38.2%; Na, 7.66%; C, 12.76%; N, 14.65%. H, 1.28%.

Example 34

Discoloration Resistance of Silver Containing Suspensions with Different Starting Ratios of Cyanurate to Silver Ions The resistance to discoloration of aqueous suspensions due to heat was examined. The suspensions were derived by maintaining different starting ratios of cyanurate anions to silver cations of stock solutions of monosodium cyanurate (0.1M) and silver nitrate (0.1M). The resulting suspensions were divided into two. One portion was saved protected from light and the other portion was steam sterilized and then subjected to continuous table lamp light exposure for at least 4 weeks. The test details and results are summarized in the table below.

Table for Ex. 34: Thermal and light stability of aqueous suspensions with different starting ratios of cyanurate and silver ions

| Test no. | Ratio (Anion/Cation) | AgNO3 0.1M (ml) | Monosodium cyanurate 0.1M (ml) | Deionized water (ml) | Observation post steam sterilization | Observation post light exposure of steam. steril. Sample |
|---|---|---|---|---|---|---|
| 1 | 0.125 | 8 | 1 | 0 | Barely discolored | Not tested |
| 2 | 0.167 | 6 | 1 | 0 | Barely discolored | Not tested |
| 3 | 0.25 | 4 | 1 | 0 | Barely discolored | Not tested |
| 4 | 0.33 | 3 | 1 | 0 | No discoloration | Not tested |
| 5 | 0.5 | 0.67 | 0.33 | 7 | No discoloration | No discoloration after 6 weeks |
| 6 | 0.75 | 0.67 | 0.44 | 6.9 | No discoloration | Not tested |
| 7 | 1 | 0.67 | 0.67 | 6.67 | No discoloration | Not tested |
| 8 | 2 | 0.67 | 1.33 | 6 | No discoloration | Not tested |
| 9 | 5 | 0.67 | 3.33 | 4 | No discoloration | No discoloration after 6 weeks |

The PP tubes with sterilized suspensions were observed after cooling them to room temperature. None of them showed discoloration. The suspension (iii) had a hint of cream color but was considered acceptable. Paper discs (dipped in the suspension and dried) subjected to ZOI assay against *Staphylococcus aureus* ATCC6538 showed clear zones of inhibition affirming the presence of antimicrobial activity. Thus, the silver cyanurate derivatives in water retain their antimicrobial activity despite exposure to high temperatures.

In a follow up experiment, the steps (iii) and (iv) were scaled up by a factor of ten. The resulting solids, disilver cyanurate and sodium silver cyanurate were recovered as white solids after discarding the supernatant liquids, washing with warm water three times to remove unreacted reagents and drying in oven at 45 C for several hours. The recovered solids were analyzed for elemental composition, the results of which are presented below.

Example 35

Preparation of Hydrogel Composition with 0.3% Hydrogen Peroxide as Active

This examples illustrates a hydrogel composition with 0.3% hydrogen peroxide that one can use to treat acne. The synthetic clay LaponiteXLG (0.8 g) was dispersed in deionized water (17 g) under stirring to yield a clear transparent gel. Glycerol (2.0 g) was hand-mixed into the gel and finally 30% hydrogen peroxide (ACS grade, Fisher Scientific) was pipetted and uniformly mixed in. In another variation, the clay was dispersed first into a solution of sodium chloride (0.02 g in 17 ml deionized water) and the remaining procedure was used as described above. The latter gel sample was applied by a human subject on acne pimples on the face each evening for 2-3 days. That resulted in substantially complete clearing of the acne pimples. In addition, the black scar on the pimple sites also reduced rapidly as the subject continued to use the gel for few more days. The subject did not experience irritation or burning sensation on the skin due to gel use. Another subject used the thixotropic gel (with silver content of 540 ppm) of Example 4 on acne pimples for 2-3 days and found the pimples cleared quickly without any sensation of burning or irritation. The subjected also noticed the black scar due to pimples faded with continued use of the gel on the affected area for few more days.

In a modification of the gel formulation, both hydrogen peroxide (~0.3% w/w) and mixed silver cyanurate (~540 ppm) were included as actives. The gel formulation sample was prepared as described in Example 4 with the exception that 0.2 ml deionized water left out. In its place, 0.2 ml 30% w/w hydrogen peroxide was added in the final step and hand-mixed to uniformity. The gel formulation appeared the same as the gel in Example 4.

Example 36

Preparation of Gel with Silver Contents of 110 ppm and 440 ppm and Corresponding Ratios of $Ag^+$ to Cyanurate Ions of 0.2 and 0.8 Respectively The gel was prepared to examine if the cyanurate anion maintained in excess during the precipitation of sodium silver cyanurate ligand complex affected the discoloration resistance to light. Thus, the gel was prepared following the procedure in Example 24 except glycerol was used in place of urea and the volumes of silver nitrate and monosodium cyanurate solutions were accordingly adjusted to reflect the desired ions ratio. The smooth slightly hazy gel (440 ppm Ag) was exposed to direct sunlight for 4.5 h without any discoloration. After 5 h, slight greying was observed so the sunlight exposure was stopped. The greyed gel sample was returned to the lab drawer overnight and re-examined the next day. The greying of the gel had reversed and the gel had become clear again. In contrast, a commercially available gel (Curad® from Medline Industries) with a silver content of 55 ppm discolored to pale yellow and after overnight in the dark did not reverse the yellow discoloration. In comparison, the gel with 110 ppm Ag and cyanurate ions five time Ag ions, did not discolor in sunlight even after 6 h when the test was terminated. The gel also did not discolor after steam sterilization. Further, the sunlight exposed steam sterilized gels (110 ppm and 440 ppm Ag) retained their antimicrobial activity as evident from clear inhibition zones from the ZOI assay employing *Staphylococcus aureus* ATCC6538 and *Pseudomonas* ATCC9027. Thus, a slight excess of cyanurate ions during the gel preparation increases the light induced discoloration resistance without affecting excellent discoloration resistance to elevated temperatures.

In a variation of the above gel composition with 440 ppm Ag, glycerol was replaced with propylene glycol to obtain a smooth hazy gel. The gel did not discolor even after 4 h of sunlight exposure. The gel gave a first hint of discoloration after 4.5 h sunlight exposure though the discoloration reversed after the gel sample was kept in the dark overnight.

In another variation of the gel, the amount of silver was set at 1100 ppm. The obtained gel was smooth but somewhat opaque. When exposed to direct sunlight, the first hint of discoloration appeared at 2 h which is quite remarkable considering a commercial gel, Normlgel Ag with 1100 ppm Ag discolors within minutes.

A comparative gel was made with 110 ppm Ag but using silver saccharinate as active and the ratio of saccharinate anions to silver ions of five. The gel discolored within 10 minutes when left exposed to sunlight.

In another variation, a gel with 110 ppm Ag was made but the ratio of cyanurate ions to silver ions was kept at one. The obtained gel was thixotropic, smooth and slightly hazy. When exposed to sunlight, the first appearance of discoloration was at 4.5 h. Surprisingly, the discoloration reversed overnight when the exposed sample was left in the dark. The gel sample registered positive antimicrobial activity against *Staphylococcus aureus* ATCC6538 and *Pseudomonas aeruginosa* ATCC9027 in ZOI assay.

Example 37

Preparation of Silver Impregnated Cotton Gauze in the Presence of Sodium Cyanurate This examples illustrates the protective effect of cyanurate anions to discoloration induced by light. A dipping solution comprising equal volumes of Tween 20 (15 g/l), sodium saccharinate (0.125M), silver nitrate (0.1M) and monosodium cyanurate (0.1M) was prepared by mixing the solution in the listed order. Two gauzes (2"×2", Medline Industries, USP Type VII) were soaked in deionized water for 15 min and squeezed to remove water and any additives from its manufacture.

In a 15 ml PP tube, ethanol (11.2 ml, 95%) was transferred and the above dipping solution (0.8 ml) was then added. The contents were vortexed and poured over the two gauzes placed in a petri-dish to soak the liquids for a few minutes. Each piece was then gently lifted from the dish to drain as much liquid out and then placed on a nylon mesh and left to dry in an oven. The finished gauze visually looked the same as an untreated piece.

When exposed to sunlight, a first hint of discoloration of the silver impregnated gauze was seen at 3 h. A gauze piece made similarly but omitting the monosodium cyanurate discolored within 0.5 h.

Example 38

Preparation of Gel with 540 ppm Ag from Sodium Cyanurate and Silver Nitrate

Using the composition of gel of Example 4, 500 g gel was made. The gel was packaged in cosmetic grade PP tubes and left at 55 C for 8 weeks for thermal aging. Each week the gel was examined for color. No discoloration was observed. The aged gel samples were tested for antimicrobial property against *Staphylococcus aureus* ATCC6538 and *Pseudomonas aeruginosa* ATCC9027 in ZOI assay and were found to be effective. The gel samples were exposed to sunlight and did not show discoloration until after 3 h.

Example 39

Preparation of Gel with 540 ppm Ag with a Mixture of Humectants

A gel sample (20 g) was prepared with a substantially identical composition as the gel in Example 4 except the glycerol was 12.5% by weight of the total humectant content with the rest being propylene glycol. No discoloration of the gel was observed until after 3 h of sunlight exposure. The discoloration seemed to have reversed its course after the sample was left in the dark overnight.

In another variation of the gel composition, the humectant was all propylene glycol. When exposed to gel, it did not discolor until the exposure duration reached 3.5 h.

In yet another variation of the gel composition, the gel was made without the use of any humectant. The resulting gel did not discolor in sunlight for 6 h when the test was stopped. However, the dried form of the gel recovered as flaky powder (from drying the gel by removing all moisture) discolored rapidly in sunlight. This was expected as the amount of silver based on the amount of Laponite XLG was nearly 1.8% wt.

In yet another variation of the gel composition, the total humectant amount was split equally between glycerol and propylene glycol. In a modification of the preparation method, the humectant and the clay was mixed first and then hydrated followed by the addition of monosodium cyanurate and silver nitrate respectively. The discoloration due to sunlight exposure was not observed until after 7 h. Thereafter, to the discolored sample (~2.5 g) in a PP tube, was added 30% w/w hydrogen peroxide. The contents were vortexed and left on the bench for 2 h when the discoloration disappeared and the gel became clear. The sample was re-exposed to sunlight for an additional 6 h with no noticeable discoloration. But with exposure, the opacity of the gel increased. Clearly the presence of hydrogen peroxide increased the discoloration resistance.

Example 40

Preparation of PVA Hydrogel Sheet Embedded with Silver Cyanurate Derivative

To 20 g solution of 10% w/w PVA (Sigma Aldrich, 85K-124K Mol. Wt, 98+% Hydrolyzed), monosodium cyanurate (1 ml, 0.1M) and silver nitrate (1 ml, 0.1M) were successively added. The silver salt solution was added in the dark. After briefly vortexing, the contents were gently centrifuged (600 rpm) for 1 min to remove bubbles. The viscous mixture was poured in a 4" dia petri-dish and subjected to 3 freeze thaw cycles (20 C/−10 C/20 C). The resulting gel piece did not show the active silver compound precipitated out or discolored. The gel piece could be stretched without breaking and could find an application as first response burn or wound contact anti-infective dressing because of its soothing feel on skin. The theoretical silver content of the piece was ~1000 ppm.

Example 41

Preparation of Gel with the Ratio of Cyanurate to Silver Ions 0.5

The rationale for preparing a gel sample of this example was to investigate the effect on light discoloration resistance when the starting ratio of cyanurate to silver ions was less than 1.0. The gel was prepared on 20 g scale following the method of Example 4 except the volume of monosodium cyanurate was half. The volume deficit was made up by adding deionized water. Even after 72 h continuous table lamp light exposure, no gel discoloration was seen.

Example 42

Preparation of Gel with Laponite XLG and NaCMC as Thickeners in Equal Proportions In this example, equal amounts of Laponite XLG and Sodium CMC were used with total thickener content of 2% w/w of the gel. The method of making the gel was similar to that of Example 3 except the clay mineral was allowed to hydrate first and then Sodium CMC and glycerol were added. An opaque white but pleasant gel was obtained.

The table lamp light exposure test revealed no discoloration of the sample even after 72 h continuous exposure.

Example 43

Discoloration Testing of Mixed Silver Cyanurate as Dry Precipitate

In a 15 ml PP tube, monosodium cyanurate (1.0 ml, 0.1M) and silver nitrate solutions (1.0 ml, 0.1M) were successively transferred to obtain a white precipitate. The suspension was vortexed briefly and washed three times with 95% ethanol. After the $3^{rd}$ washing, the suspension was poured into a petri-dish and dried at 37 C for ~4 h. Initially, the solid layer was exposed to table lamp light for 1 h (no discoloration) and then left in the sunlight every day for a total exposure of ~24 h. No discoloration of the solids in the petri-dish was observed. This result is quite remarkable for an antimicrobial silver compound.

Example 44

Discoloration Resistance of SilverSept® Commercial Wound Care Product

To further test discoloration resistance to light, example commercial products were purchased and exposed to light to enable a comparison to the silver cyanurate derivate compounds and products thereof as described herein. In a capped glass dram vial ~2-4 g of SilverSept® gel (Lot 0J1215S) was exposed to table lamp light. At 4 h, the first hint of yellow appeared and after 24 h, the gel imparted distinct yellow brown discoloration. Thus, SilverSept® gel that has ~100 ppm silver demonstrated poor discoloration resistance to light compared to the gel prototypes based on silver cyanurate derivative compounds.

Example 45

Discoloration Resistance Testing of Gel Prototypes with Silver Content ~540 ppm & Comparison with Commercial Silver Wound Gels All gels were made by following the procedure of Example 4 unless stated otherwise. Appropriate quantities of humectants as indicated in the table were added followed by monosodium cyanurate and silver nitrate solution. In the case of gel sample #3, a slightly different method was employed. First, the cyanuric acid in an amount of 1:1 mole ratio with respect to silver nitrate amount (1 ml, 0.1M) was dissolved in water. Then, Laponite XLG was dispersed, silver nitrate solution was dripped in and finally the humectant propylene glycol was added. The gel samples including commercial products were placed in 15 ml PP tubes and exposed to appropriate light conditions and examined for discoloration. The results are tabulated below.

Table for Ex. 45: Discoloration resistance test results of gel prototypes with silver content ~540 ppm.

| Sample ID | Laponite XLG % w/w | Glycerol % w/w | Propylene Glycol % w/w | TLE | SLE | Results |
|---|---|---|---|---|---|---|
| 1 | 4 | 7.5 | 2.5 | 24 h/test stopped | Not tested | No discoloration |
| 2 | 4 | 2.5 | 7.5 | 24 h/test stopped | Not tested | No discoloration |
| 3 | 4 | 0 | 10 | Not tested | 0.5 h | Discoloration reverses in dark overnight |
| 4 | 4 | 10 | 0 | Not tested | 4 h | No discoloration |
| 5 | 4 | 10 | 0 | Not tested | 6 h | Discoloration reverses in dark overnight |
| 6 | 4 | 10 | 0 | Not tested | 6 h | Discoloration reverses in dark after 3 days |
| 7 | 4 | 0 | 10 | Not tested | 6 h | No discoloration |
| 8 | 4 | 5 | 5 | Not tested | 10 h | No discoloration & no delayed discoloration |
| SilverSept | | | | Not tested | <0.25 h | Discolored brown, no reversal |
| Silvasorb | | | | Not tested | <0.25 h | Discolored brown, reversed partially after 3 days |
| Normlgel Ag | | | | Not tested | <0.25 h | Discolored brown, no reveral |

TLE: Table lamp light exposure,
SLE: Sunlight exposure,
Duration shown is the time of onset of discoloration

Example 46

Antimicrobial Activity Testing of Suspensions of Silver Cyanurate Compounds

The suspensions have potential use in preventing or inhibiting the growth of microorganisms that may contaminate the contact lens when held overnight in plastic lens case. Such contamination may be due to improper handling of lens or lens cases or lens cleaning solutions. To eliminate the risk of harm to the lens wearer due to potential microbial contamination, a few drops of liquid compositions comprising silver are added to the cleaning solution containing the lens in the case and left overnight. As one example, the silver will go to work killing any microorganisms that could have contaminated the case or the solution.

To simulate this real life situation, the following experiment was performed in the lab. In a 50 ml PP tube, 10 ml monosodium cyanurate solution (0.001M) were added and then 10 ml silver nitrate solution (0.001M) were added dropwise (with cyanurate to silver ions ratio ~1.0, the active compound was mixed silver cyanurate). No immediate precipitation was seen. So the tube was left overnight in the dark to complete the reaction. Next day, very fine particles were observed in the tube when the contents were vortexed. The theoretical amount of silver in the suspension was ~55 ppm. Using this stock suspension, four equal volumes of liquid compositions with silver content of ~50, ~25 and ~10 and ~0 ppm with 5% TSB were prepared in four separate 5 ml PS tubes. To each tube, the same size of inoculum of Staphylococcus aureus ATCC6538 was added. The tubes were incubated at 37 C overnight. The next day (~20 h elapsed time) the known liquid aliquots from the tubes were plated on agar plates and incubated at 37 C for 24 to 48 h to grow colonies. The zero time inoculum strength in cfu/ml was determined by plating the inoculum and incubating the plates at 37 C over 24 to 48 h. The surviving colonies from samples with silver were counted and from the zero count inoculum value (~1e5 cfu/ml), the log reduction associated with liquids with 50, 25 and 10 ppm silver was calculated.

The results showed no surviving colonies in any tube containing silver indicating greater than 99.99% reduction.

Example 47

Preparation of Antimicrobial Petroleum Based Cream with Silver Content ~540 ppm The antimicrobial compound may be added to a petroleum based cream. The first step was to prepare the mixed silver cyanurate suspension in a 15 ml PP tube by successively pipetting stock solutions of monosodium cyanurate (0.5 ml, 0.1M) and silver nitrate (0.5 ml, 0.1M) under dim light conditions. After waiting for 15 min.~1 drop of Tween 20 emulsifier was added to the suspension and vortexed to uniformity. To a plastic cup (~100 ml), 10 g petroleum jelly (Vaseline® brand from a local store) was transferred. Next, with the help of a transfer pipet, the suspension was dripped into the cup a few drops at a time. After each addition of the suspension aliquot, the jelly was vigorously hand-mixed to blend in the silver composition. At the end, the jelly turned to an opaque white cream that was very smooth to feel. No discoloration of the cream as compared to the light protected cream sample was seen after nearly 4 weeks of exposure to table lamp light. The cream was found to be active against Staphylococcus aureus ATCC6538 in ZOI assay.

Example 48

Preparation of Zinc Oxide Based Antimicrobial Ointment with Silver Content ~540 ppm The procedure in Example 47 was repeated with Desitin® ointment in place of petroleum jelly. The resulting cream showed some discoloration in the form of grey coating on the exposed surface after 1 week of exposure to lamp light though the light protected sample was unchanged in color from when made fresh. The grey coating was on the surface with the bulk of the gel unchanged. Given that the ointment composition was not optimized for the presence of mixed silver cyanurate active compound, the discoloration due to greying was not entirely unexpected. Nonetheless, it took over a week for visible discoloration that indicated sufficient resistance of the silver active in Desitin® ointment environment. In ZOI assay using *Staphylococcus aureus* ATCC6538 the ointment was found to be antimicrobial.

Example 49

(Prophetic) Mixed Silver Cyanurate Comprising Adhesive Formulation

An adhesive formulation similar to that example disclosed in paragraph [206] US 2009/0035342 is prepared with the following modification. Instead of employing 1M solution, stock solutions of monosodium cyanurate and silver nitrate of 0.1M are used. The rest of the proportions of all chemicals are the same. The resulting adhesive film comprising in situ formed mixed silver cyanurate is expected to exert antimicrobial activity and withstand discoloration by heat and light.

Example 50

(Prophetic) Preparation of Silicone Catheter Coated with a Coating Comprising Mixed Silver Cyanurate A curable silicone coating is prepared according to the method disclosed in Example 23 US 2009/0035342 with some modifications as follows. A suspension of mixed silver cyanurate is prepared by mixing 0.2 ml each of 0.1M stock solutions of silver nitrate and monosodium cyanurate. The suspension is diluted with THF (8 ml) and poured into the 2 part silicone coating mixture prepared in the same proportions as described therein. Catheter stems are coated following the described procedure and cured employing the same thermal profile to yield silicone catheter stems coated with a coating comprising silver active cyanurate compound. The coated stems are expected to be antimicrobial and to resist discoloration by light and heat.

Example 51

(Prophetic) Preparation of Flexible PU Foam Impregnated with Mixed Silver Cyanurate Flexible medical grade PU foam pieces (~1"×1" squares and ~2 mm thick) similar to those disclosed in Example 15 of US 2009/0035342 are soaked with a silver cyanurate suspension prepared as follows. In a 15 ml PP tube, monosodium cyanurate solution (0.25 ml, 0.1M) is added, followed by silver nitrate solution (0.25 ml, 0.1M) under dark conditions. The resulting white suspension is vortexed briefly and transferred to a 50 ml PP tube with the help of transfer pipet. The 15 ml PP tube is rinsed with deionized water (5 ml) and content transferred to 50 ml PP tube. Finally more deionized water is added to the suspension in 50 ml PP tube for a total volume of 20 ml. In a shallow glass dish, four foam pieces are placed and the suspension with silver compound is poured over the pieces. The pieces are allowed to absorb the suspension over 5 min. Then each piece is separately blotted on a folded Bounty® paper to remove excess liquid and then transferred to a nylon mesh to dry in an oven at 45 C over several hours. The pieces are expected to exhibit broad spectrum antimicrobial activity and are expected to resist discoloration by heat and light.

Example 52

Preparation of Cellulose/Polyester/Rayon Gauze Pads Impregnated with Sodium Silver Cyanurate Ligand Complex Two pieces single ply (~1"×1" squares) sheet of hospital grade gauze pads made of cellulose/polyester/rayon blend (J&J Red Cross® brand Lot 2631A) were placed in a petri-dish. A suspension of silver cyanurate derivative compound was prepared and dripped evenly over the pieces with the help of a transfer pipet (~0.5 ml/piece). The suspension was made by adding silver nitrate solution (2 ml, 0.02M) to monosodium cyanurate solution (2 ml, 0.1M) and thoroughly vortexing the same. Each suspension soaked piece was blotted on a folded Bounty® paper and dried in an oven at 45 C for 30 min. There was no visible difference between the silver impregnated gauze sheet and the virgin gauze material. No discoloration of the silver impregnated piece was observed after 6 h of direct sunlight exposure or steam sterilization in a foil pouch. In appearance it looked the same as the sample piece that was protected from light and heat. The sunlight exposed piece was tested for antimicrobial activity against *Staphylococcus aureus* ATCC6538 in a ZOI assay and was found to be strongly effective.

As described herein, the methods according to the present disclosure include methods for making an antimicrobial composition with a silver cyanurate active agent, where the methods comprise: combining a viscosity enhancing agent and a water based solvent to yield a viscous gel; and adding a metal cyanurate solution and a soluble silver salt solution to the viscous gel, where the metal cyanurate solution and the soluble silver salt solution react to form the silver cyanurate active agent. As further described above, this reaction may occur in situ. In some example, the methods further comprise adding a humectant to the viscous gel, where the humectant is one or more of glycerol, propylene glycol, polypropylene glycol, urea, polyethylene glycol, and sodium lactate. In other examples, the methods may comprise optionally adding a coloring agent to the antimicrobial composition, where the coloring agent is one of a water soluble dye, a copper-amino acid complex, and methylene blue. In still other examples, the methods may comprise optionally adding a skin enhancing additive to the antimicrobial composition, where the skin enhancing additive includes one or more of an oil, a fragrance, a moisturizing agent, an emollient, a toning agent, and a surfactant. The methods may further comprise optionally adding a buffer to the viscous gel and adjusting a pH of the antimicrobial composition to a range of 6 to 8, although other pH ranges may be desirable based on a particular product or application of the methods. In some instances, the methods may include pre-mixing the metal cyanurate solution and soluble silver salt solution prior to addition to the viscous gel.

With regard to the reagents used in the methods, the viscosity enhancing agent that forms the viscous gel may be one or more of a synthetic clay mineral that includes Laponite®, a natural clay mineral, a cellulose ether selected from the group consisting of hydroxyethyl cellulose, hydroxypropyl cellulose, hydroxyethyl cellulose, hydroxypropyl methyl cellulose, and sodium carboxymethyl cellulose, polyacrylate, a natural gum, a chemically modified natural gum, a chemically modified cellulose ether with an aliphatic chains, a synthetic gum, polyvinyl alcohol, polyvinyl pyrrolidone, polyacrylamide, and a polyaminoacid that includes one of polyaspartate and polyglutamate. The metal cyanurate solution may include one of sodium cyanurate, potassium cyanurate, lithium cyanurate, calcium cyanurate, magnesium cyanurate, barium cyanurate, copper cyanurate, zinc cyanurate, aluminum cyanurate, and ammonium cyanurate. The soluble silver salt solution may include one of silver nitrate, silver acetate, silver lactate, silver citrate, silver sulfate and silver phosphate. According to the present disclosure, the silver cyanurate active agent may be one or more of $AgNO_3 \cdot C_3N_3(NH_2)_3$, $C_3N_3(NH_2)_2NAg_2$, Ammeline-$AgNO_3$, Ammelide-$AgNO_3$, Monosilver cyanurate ($C_3N_3H_2O_3Ag$), Disilver cyanurate ($C_3N_3HO_3Ag_2$), Trisilver cyanurate ($C_3N_3O_3Ag_3$), a sodium silver cyanurate ligand complex $Na[Ag(C_3N_3H_2O_3)_2]$, a potassium silver cyanurate ligand complex $K[Ag(C_3N_3H_2O_3)_2]$, a mixed salt of $NaAgC_3N_3HO_3$, a mixed salt of $NaAg_2C_3N_3O_3$, a mixed salt of $KAgC_3N_3HO_3$, a mixed salt $KAg_2C_3N_3O_3$, and a hydrated species thereof, wherein an amount of silver in the silver cyanurate active agent may be between 10 and 5500 ppm based on a weight of the antimicrobial composition.

The present disclosure further relates to antimicrobial compositions based on the silver compounds described. Thus, according to the present disclosure, an antimicrobial compound may comprise silver with an s-triazine ring. The antimicrobial compound may be included within an aqueous clear gel, where the aqueous clear gel with the antimicrobial compound is resistant to discoloration via one or more of light and heat. In some examples, the antimicrobial compound is included within a solid substrate. For example, the solid substrate may be selected from the group consisting of a talc powder, a zinc oxide powder, a titanium oxide powder, a bone powder, an inorganic porous support, a ceramic, a metal, an oxide, a pellet, a flexible foam, and a short fiber, although other possibilities may also be possible. In other examples, the antimicrobial compound is blended into a surface coating of a medical device. However, the antimicrobial compound may also be embedded within one or more of a woven and non-woven matrix. For example, the woven matrix may comprise one or more of cellulose, polyester, rayon and blends thereof (e.g., a wound dressing comprising the antimicrobial compound). As another example, the non-woven matrix may comprise fibers of one or more of alginate and cellulose (e.g., a cotton gauze and an absorbent paper that includes the antimicrobial compound). In still other examples, the antimicrobial compound may be included in a petroleum based cream, a suspension, a solution, a bioadhesive, a polymer solution, a lotion, an emulsion, an emulgel, a salve, an ointment, a sprayable liquid, a latex, a paste, an oily suspension, a water soluble polymeric films, and a water-insoluble film capable of the sustained release of antimicrobial silver.

One particular example of the present disclosure includes a clear topical hydrogel comprising an antimicrobial silver cyanurate active agent produced according to the methods disclosed. To enable topical application, the hydrogel is a thixotropic hydrogel that may have a yield stress in a range of 0 to 1000 Pa. Moreover, the hydrogel is inert to light and heat. In this way, the hydrogel may resist discoloration due to exposure to one or more of light and heat. The hydrogel comprising the antimicrobial active agent may further allow a skin color to be maintained in response to the topical application of the hydrogel to skin. As one example, an amount of silver in the hydrogel is between 50 and 1000 ppm based on a weight of the hydrogel.

Methods of treatment are further possible using the hydrogel just described. Thus, methods based on applying the clear topical hydrogel comprising an antimicrobial compound with a silver cyanurate active agent, to an individual are possible. As such, application of the gel may reduce a risk of infection due to HIV during sexual contact, wherein the individual is identified as an HIV uninfected individual. However, other applications are possible, and the gel may also be applied to an individual to treat a dermal condition, where the dermal condition is one or more of an acute wound, a chronic wound, a first degree burn, a second degree burn, a minor cut, a wound located on a mucous membrane, acne, rosacea, jock itch, and athlete's foot.

The reading of the description by those skilled in the art would bring to mind many alterations and modifications without departing from the spirit and the scope of the description. It is to be understood that the configurations and/or approaches described herein are exemplary in nature, and that these specific embodiments or examples are not to be considered in a limiting sense, because numerous variations are possible. The specific routines or methods described may represent one or more of any number of data collection strategies. As such, various acts illustrated may be performed in the sequence illustrated, in other sequences, in parallel, or in some cases omitted. Likewise, the order of the above-described processes may be changed.

It will be appreciated that the configurations and routines disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and sub-combinations regarded as novel and nonobvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An antimicrobial composition, comprising:
    a mixture of disilver cyanurate ($C_3N_3HO_3Ag_2$) and a sodium silver cyanurate ligand complex $Na[Ag(C_3N_3H_2O_3)_2]$;
    a viscosity enhancing agent between 0.10% and 10% of a weight of the composition; and
    a humectant between 1% and 40% of the weight of the composition,
    wherein the composition is inert to heat and light.

2. The antimicrobial composition of claim 1, where the antimicrobial composition is included within an aqueous clear gel, and the aqueous clear gel with the antimicrobial composition is resistant to discoloration via one or more of light and heat.

3. The antimicrobial composition of claim 2, where the antimicrobial composition is included within a solid substrate.

4. The antimicrobial composition of claim 3, wherein the solid substrate is selected from the group consisting of a talc powder, a zinc oxide powder, a titanium oxide powder, a bone powder, an inorganic porous support, a ceramic, a metal, an oxide, a pellet, a flexible foam, and a short fiber.

5. The antimicrobial composition of claim 1, where the antimicrobial composition is one of blended into a surface coating of a medical device and embedded within one or more of a woven and/or non-woven matrix.

6. The antimicrobial composition of claim 5, wherein the woven matrix comprises one or more of cellulose, polyester, rayon and/or blends thereof, and wherein the non-woven matrix comprises fibers of one or more of alginate and/or cellulose.

7. The composition of claim 1, where the composition is at least one of:
a suspension, a solution, a bioadhesive, a lotion, a hydrogel, an emulsion, an emulgel, a salve, an ointment, a sprayable liquid, a paste, and/or an oily suspension;
wherein the disilver cynaurate comprises a hydrated species, and wherein the sodium silver cyanurate ligand complex comprises a hydrated species.

8. A clear topical hydrogel, comprising: an antimicrobial composition comprising a mixture of disilver cyanurate ($C_3N_3HO_3Ag_2$) and a sodium silver cyanurate ligand complex ($Na[Ag(C_3N_3H_2O_3)_2]$).

9. The clear topical hydrogel of claim 8, where an amount of silver in the hydrogel is between 50 and 1000 ppm based on a weight of the hydrogel.

10. The composition of claim 1, wherein the viscosity enhancing agent includes one or more of a synthetic clay mineral, a natural clay mineral, a cellulose ether selected from the group consisting of hydroxyethyl cellulose, hydroxypropyl cellulose, hydroxypropyl methyl cellulose, and sodium carboxymethyl cellulose, polyacrylate, a natural gum, a chemically modified natural gum, a chemically modified cellulose ether with an aliphatic chains, a synthetic gum, polyvinyl alcohol, polyvinyl pyrrolidone, polyacrylamide, and/or a polyaminoacid that includes one of polyaspartate and polyglutamate.

11. The composition of claim 1, wherein the humectant includes one or more of glycerol, propylene glycol, polypropylene glycol, urea, polyethylene glycol, and/or sodium lactate.

12. The composition of claim 1, further comprising:
a skin enhancing additive, wherein the skin enhancing additive includes at least one of an oil, a fragrance, a moisturizing agent, an emollient, a toning agent, and/or a surfactant.

13. The composition of claim 1, further comprising:
a buffer, where the buffer maintains the composition between a pH of 6 to 8.

14. The composition of claim 1, wherein the composition has a yield stress in a range of 0 to 1000 Pa.

15. The composition of claim 1, wherein an amount of silver in the composition is between 10 and 5500 ppm based on the weight of the composition.

16. The composition of claim 1, further comprising:
a coloring agent, where the coloring agent is one of a water soluble dye, a copper-amino acid complex, and/or methylene blue.

17. An antimicrobial composition, comprising:
a mixture of disilver cyanurate ($C_3N_3HO_3Ag_2$) and a sodium silver cyanurate ligand complex $Na[Ag(C_3N_3H_2O_3)_2]$, where the composition is inert to heat and light, and wherein an amount of silver is between 10 and 5500 ppm relative to a weight of the composition; and
a substrate.

18. The composition of claim 17, wherein the substrate is a solid substrate consisting of one of at least a talc powder, a zinc oxide powder, a titanium powder, a bone powder, an inorganic porous support, a ceramic, a metal, an oxide, a pellet, a flexible foam, and/or a short fiber.

19. The composition of claim 17, wherein the substrate is a woven matrix consisting of one of at least cellulose, polyester, rayon, and/or blends thereof.

20. The composition of claim 17, wherein the substrate is a non-woven matrix consisting of fibers of one or more of alginate and/or cellulose.

21. The composition of claim 17, wherein the substrate is at least one of:
a petroleum based cream, a latex, a water soluble polymeric film, and/or a water-insoluble film.

22. An antimicrobial composition, comprising:
a mixture of disilver cyanurate ($C_3N_3HO_3Ag_2$) and a sodium silver cyanurate ligand complex $Na[Ag(C_3N_3H_2O_3)_2]$, where the composition exhibits no visible sign of discoloration after a steam sterilization cycle comprising 122° C. for fifteen minutes, and where the composition is inert to light.

23. The composition of claim 22, further comprising a viscosity enhancing agent between 0.10% and 10% of a weight of the composition, and wherein the viscosity enhancing agent includes one or more of a synthetic clay mineral, a natural clay mineral, a cellulose ether selected from the group consisting of hydroxyethyl cellulose, hydroxypropyl cellulose, hydroxypropyl methyl cellulose, and sodium carboxymethyl cellulose, polyacrylate, a natural gum, a chemically modified natural gum, a chemically modified cellulose ether with an aliphatic chains, a synthetic gum, polyvinyl alcohol, polyvinyl pyrrolidone, polyacrylamide, and/or a polyaminoacid that includes one or more of polyaspartate and/or polyglutamate.

24. The composition of claim 22, further comprising a humectant between 1% and 40% of a weight of the composition, and wherein the humectant includes one or more of glycerol, propylene glycol, polypropylene glycol, urea, polyethylene glycol, and/or sodium lactate.

25. The composition of claim 22, further comprising a substrate.

26. The composition of claim 25, wherein the substrate is one or more of a solid substrate consisting of one of at least a talc powder, a zinc oxide powder, a titanium powder, a bone powder, an inorganic porous support, a ceramic, a metal, an oxide, a pellet, a flexible foam, and/or a short fiber; a woven matrix consisting of one of at least cellulose, polyester, rayon, and/or blends thereof, a non-woven matrix consisting of fibers of one or more of alginate and/or cellulose; and/or a petroleum based cream, a latex, a water soluble polymeric film, and/or a water-insoluble film.

* * * * *